(12) United States Patent
Anazawa et al.

(10) Patent No.: US 6,242,193 B1
(45) Date of Patent: Jun. 5, 2001

(54) APPARATUS FOR DETERMINING BASE SEQUENCE OF NUCLEIC ACID

(75) Inventors: Takashi Anazawa, Kokubunji; Kazunori Okano, Shiki; Chihiro Uematsu, Kawasaki; Hideki Kambara, Hachioji, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/567,270

(22) Filed: May 9, 2000

Related U.S. Application Data

(63) Continuation of application No. 09/355,567, filed on Jul. 30, 1999, now Pat. No. 6,136,543.

(51) Int. Cl.[7] ............... C12Q 1/68; C12P 19/34; C07H 19/00; C07H 21/00; C07H 21/02
(52) U.S. Cl. ............... 435/6; 435/91.1; 435/91.2; 536/22.1; 536/23.1; 536/24.3; 536/24.33; 536/25.3
(58) Field of Search ............... 435/6, 91.1, 91.2; 536/22.1, 23.1, 24.3, 24.33, 25.3

(56) References Cited

U.S. PATENT DOCUMENTS

| | | | |
|---|---|---|---|
| 4,786,170 | 11/1988 | Groebler et al. | 356/318 |
| 4,828,979 | 5/1989 | Klevan et al. | 435/6 |
| 4,893,886 | 1/1990 | Ashkin et al. | 350/1.1 |
| 5,258,506 | 11/1993 | Urdea et al. | 536/23.1 |

FOREIGN PATENT DOCUMENTS

| | | |
|---|---|---|
| 2-57978 | 2/1990 | (JP) . |
| 2-91545 | 3/1990 | (JP) . |
| 2-269936 | 11/1990 | (JP) . |
| 4-505251 | 9/1992 | (JP) . |
| WO90/13666 | 11/1990 | (WO) . |

OTHER PUBLICATIONS

Journal of Biomolecular Structure and Dynamics, vol. 7, No. 2, 1989, pp. 301–309, Jelt et al.
Electrophoresis, vol. 13, 1992, pp. 495–499, Nishikawa et al.
Electrophoresis, vol. 13, 1992, pp. 616–619, Ansorge et al.
Electrophoresis, vol. 13, 1992, pp. 574–582, Slater et al.
Science, vol. 254, 1991, pp. 59–67, Hunkapiller et al.
Annual Rev. Biophys. Biophys Chem. 1989, vol. 18, pp. 239–270, McCray et al.
Science, vol. 238, 1987, pp. 336–341, Prober et al.
Journ. American Chem. Soc., vol. 110, 1988, pp. 7170–7177, Walker et al.
Analytical Biochemistry, vol. 23, 1996, pp. 166–174, Wiemanu et al.
Nature, vol. 374, Apr. 1995, pp. 555–559, Fumatsu et al.
Science, vol. 271, Feb. 1996, pp. 795–799, Smith et al.
Optics Letter, vol. 11, No. 5, May 1986, pp. 288–290, Ashkin et al.
Science, vol. 271, Mar. 1996, pp, 1835–1837, Strick et al.

*Primary Examiner*—Jezia Riley
(74) *Attorney, Agent, or Firm*—Mattingly, Stanger & Malur, P.C.

(57) ABSTRACT

A single molecule of single-stranded sample DNA (7) having a bead (5) at one end and a magnetic bead (6) at the other end is extended and fixed in the field of view of a fluorescent microscope by using a magnetic force (11) and a laser trap (3), and a primer (8) is bonded thereto, followed by elongation reaction (10) using polymerase. Only a single chemically modified nucleotide (9) labeled with at least one fluorophore which varies depending on the kind of the base is incorporated. Only the single fluorophore incorporated is measured as a fluorescence-microscopic image by evanescent irradiation (13) with exciting laser beams, and the kind of the base is determined from the kind of the fluorophore. The fluorophore labeling the nucleotide incorporated is released by evanescent irradiation (13) with ultraviolet laser beams (2), and the next nucleotide is incorporated. DNA sequencing is carried out by repeating the above procedure. The base sequence determination can be carried out by using the single DNA molecule, so that a DNA base sequence of hundreds kilos or more bases can be efficiently determined.

9 Claims, 36 Drawing Sheets

FIG. 3
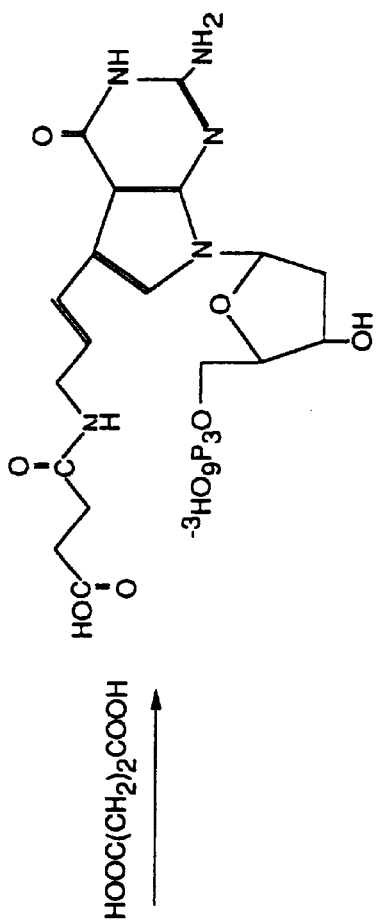
HOOC(CH₂)₂COOH
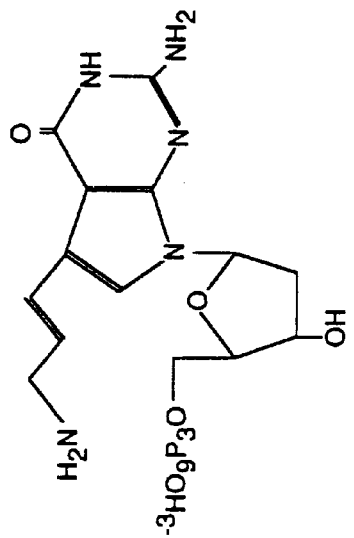

FIG. 4
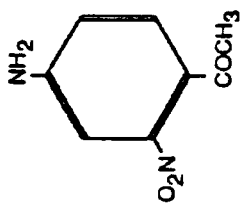
↑ Fe | H+
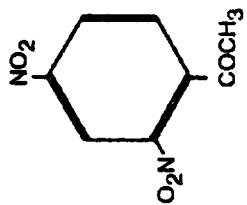
↑ HNO₃ | H+
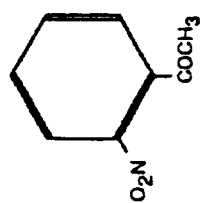

FIG. 5
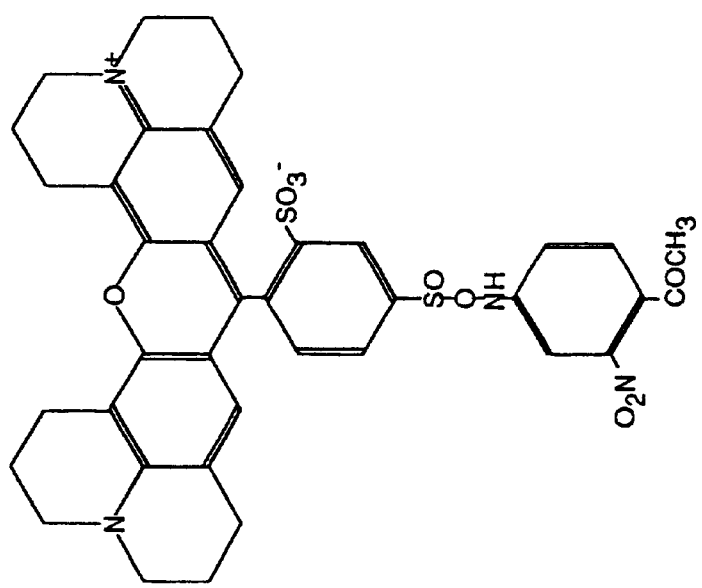
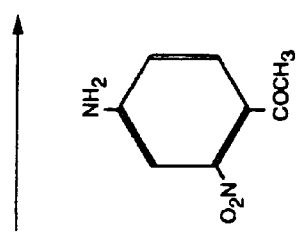
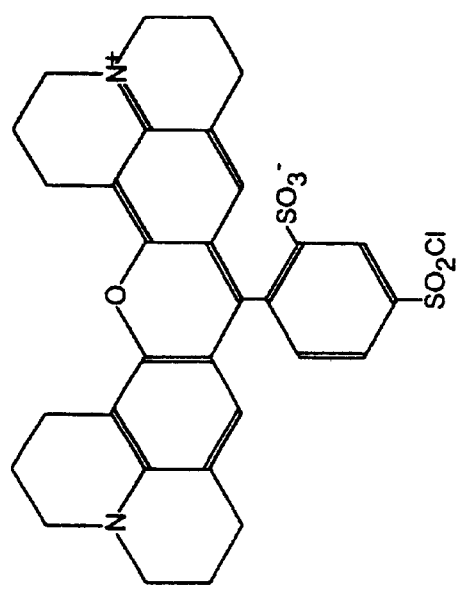

APPARATUS FOR DETERMINING BASE SEQUENCE OF NUCLEIC ACID

This is a continuation application of U.S. Ser. No. 09/355,567, filed Jul. 30, 1999 now U.S. Pat. No. 6,136,543.

TECHNICAL FIELD

This invention relates to an apparatus for analysis of DNA, RNA and the like. In particular, it relates to an apparatus effective in determination of the base sequences of DNA and RNA or analysis of restriction fragments and specific fragments.

BACKGROUND ART

Techniques for analysis of DNA, RNA and the like have become important in the medical and biological fields including gene analysis and genetic diagnosis. Both the determination of the base sequences of DNA or RNA and the analysis of restriction fragments or specific fragments are based on separation carried out on the basis of molecular weight by electrophoresis. In this case, a fragment or a group of fragments is previously labeled with a radioactive or fluorescent label, and a development pattern of separation on the basis of molecular weight is measured after or during the electrophoresis of the labeled fragment or fragments, whereby the fragment or fragments are analyzed. The need for, in particular, a DNA sequencing apparatus has recently increased in relation to genome analysis, so that the development of the apparatus is in progress. DNA sequencing using a fluorophore label is explained below. Dideoxy reaction according to the Sanger method is carried out before electrophoretic separation. An oligonucleotide having a length of 20 bases which is complementary to the known base sequence portion of a sample DNA to be analyzed is synthesized and then labeled with a fluorophore. This oligonucleotide is complementarily bonded as a primer to about $10^{-12}$ mol of the sample DNA, and the elongation reaction of a complementary strand is carried out with polymerase. In this case, as substrates, there are added four deoxynucleotide triphosphates, i.e., deoxyadenosine triphosphate (dATP), deoxycytidine triphosphate (dCTP), deoxyguanosine triphosphate (dGTP), deoxythymidine triphosphate (dTTP), as well as dideoxyadenosine triphosphate (ddATP). When ddATP is incorporated by the elongation of the complementary strand, the complementary strand is not further elongated, so that fragments of various lengths terminated by adenine (A) are prepared. The same reaction as above is independently carried out except for adding each of dideoxycytidine triphosphate (ddCTP), dideoxyguanosine triphosphate (ddGTP) and dideoxythymidine triphosphate (ddTTP) in place of ddATP. The primers used in these reactions, respectively, have the same base sequence but are labeled with four kinds of fluorophores, respectively, which can be distinguished from one another by fluorescence separation into spectral components.

The 4 kinds of the reaction products thus obtained are mixed to prepare fragments which are complementary to the sample DNA, have a length up to about 1000 bases, differ in length by steps of 1 base, and have any of the 4 kinds of the fluorophore labels, depending on the kind of the terminal base. For each of the fluorophore labels, the amount of fragments having each length (number of bases) is about $10^{-15}$ mol. Then, the samples prepared are separated by electrophoresis with a resolving power of 1 base. In the electrophoresis, there is widely used a slab gel obtained by polymerizing acrylamide between two glass plates about 0.3 mm apart from each other. When the samples are placed at the upper end of the slab gel and an electric field is applied to the upper and lower ends of the slab gel, the samples migrate toward the lower end while being separated. When a position about 30 cm below the upper end is irradiated with laser beams while carrying out the electrophoresis, the fluorophore-labeled fragments separated pass the laser irradiation position to be subjected to excitation, in the order of increasing length. By measuring the emitted fluorescence while separating it into spectral components with a plurality of filters, the kinds of terminal bases of all the fragments can be determined in the order of increasing fragment length, from the change with time of the fluorescence intensity of the four kinds of the fluorophores. Since the thus determined order of the bases is complementary to that of the sample DNA, the base sequence of the sample DNA can be determined.

There have been proposed several novel DNA sequencing methods using no electrophoresis. In a first prior art, in carrying out the elongation reaction of a complementary strand by using polymerase and a sample DNA as template, the 4 kinds of the substrates are added one by one, and the amount of the substrates incorporated into the complementary strand is determined at each stage by utilizing light absorption or fluorescence, to determine the base sequence of the sample DNA (JP-A-4-505251). In a second prior art, the elongation reaction of a complementary strand is carried out by using polymerase, a sample DNA as template and the 4 kinds of the substrates labeled with different labels, respectively, after which bases are released one by one from the 3'-end of the thus synthesized complementary strand with exonuclease, and the labels of the released bases, respectively, are measured in turn to determine the base sequence of the sample DNA (Journal of Biomolecular Structure & Dynamics 7, 301–309 (1989)). In a third prior art, the base sequence of a sample DNA is determined by repeating a cycle consisting of a step of carrying out DNA polymerase reaction by using four dNTP derivatives (MdNTPs) which have a detectable label and can be incorporated into a template DNA as substrates for DNA polymerase to stop DNA strand elongation reaction, owing to the presence of their protecting group, a step of detecting the incorporated MdNTP, and a step of returning this MdNTP to its original state at which the elongation is possible. In this prior art, the DNA strand elongation is stopped every time the DNA strand is elongated by one base, and the enzyme and the substrates are removed from a system (a solution) containing the template, a primer and the MdNTPs, after which the MdNTP incorporated is detected, and the protecting group (and the label) of the MdNTP incorporated into the template are removed to return this MdNTP to its original state at which the DNA strand elongation is possible (Japanese Patent Application No. 2-57978). These proposals, however, set forth mere ideas at present and no practical application thereof has been reported.

DISCLOSURE OF THE INVENTION

In DNA sequencing methods which have been put to practical use, separation on the basis of molecular weight is carried out by electrophoresis. For DNA sequencing, the resolving power for the separation on the basis of molecular weight should be a length of one base. Usually, the resolving power of the electrophoresis decreases with an increase of the length (number of bases) of DNA fragments to be separated. That is, even if a DNA fragment having a length of 50 bases and that having a length of 51 bases can be separated from each other on the basis of the length difference of one base, a DNA fragment having a length of 500 bases and that having a length of 501 bases cannot always be separated from each other on the basis of the length difference of one base. The length (number of bases) at separation limit which indicates the limit of the length (number of bases) within which a resolving power of one base can be attained, is determined by the electrophoresis conditions, i.e., the composition of a medium for separation, the length of electrophoresis lanes and the intensity of electric field. Various optimizations have been carried out for increasing the length (number of bases) at separation limit, but there is no report that the limit exceeds 1000 bases (Electrophoresis 13, 495–499 (1992) and Electrophoresis 13, 616–619 (1992)). There has been theoretically explained the fact that the length (number of bases) at separation limit is at most 1000 bases (Electrophoresis 13, 574–582 (1992)). That is, when electrophoresis is employed, the length of a base sequence which can be determined from one kind of sample DNA is at most 1000 bases. On the other hand, in large-scale base sequence determination represented by genome analysis, the length (number of bases) at separation limit definitely affects the analysis efficiency (Science 254, 59–67 (1991)). For example, (a YAC clone, a typical large clone) has a length of about 1 M bases, and hence when its successive portions each having a length of 1000 bases are analyzed, at least 1000 samples should be analyzed. However, successive fragments each having a length of 1000 bases can be prepared neither too far from nor too near the end of a long DNA. In practice, random fragments are prepared and then analyzed at random, and the original long DNA base sequence is reconstructed by utilizing the overlap of the base sequences of the fragments with one another. This method is called a shot gun method and is most widely adopted for genome analysis. It, however, is disadvantageous in that the same base sequence should be repeatedly analyzed because the random fragments should have overlaps which permits the reconstruction.

The degree of this overlapping is called redundancy and increases with a decrease of a length (number of bases) at which base sequence determination can be carried out at a time, i.e., the length (number of bases) at separation limit in electrophoresis. When the length (number of bases) at separation limit is 1000 bases, the redundancy is about 10. That is, it is necessary to determine base sequences having a total length of 10 times the length of a DNA whose base sequence is to be determined. Therefore, about 10,000 samples should be analyzed for determining a base sequence having a length of 1 M bases. The number of samples which can be analyzed with a DNA sequencing apparatus is at most 100 per day. Thus, it takes at least 100 days to determine the whole base sequence having a length of 1 M bases with the apparatus. For effectively carrying out genome analysis or genetic diagnosis which will acquire greater importance, there is required a technique for achieving in several days the determination of a base sequence having a length of 1 M bases.

Another problem in the prior art is that a large number of sample DNAs are necessary for base sequence determination. For carrying out dideoxy reaction by the Sanger method, about $10^{-12}$ mol of each sample DNA is usually necessary. Therefore, the sample DNAs should be previously purified and amplified by techniques such as cloning and PCR. These techniques require much time and labor and hence constitute a remarkable rate-limiting step in the progress of genome analysis. For efficiently carrying out genome analysis and genetic diagnosis, there is required a technique which permits base sequence determination by the use of a small amount of sample DNAS, ultimately a single DNA molecule. The proposed DNA sequencing methods, however, involve the following problems.

In the first prior art, since the 4 kinds of the nucleotide substrates are added one by one, it is necessary to change repeatedly the composition of a solution in which the elongation reaction of a complementary strand is carried out. In addition, when the kind of base in the solution is changed, washing is necessary for preventing the presence of foreign bases. Therefore, at least 8 runs of solution replacement are needed per cycle. On an average, one base is usually determined by one cycle, so that the 8 runs of solution replacement considerably lowers the base sequence determination rate. A key problem in the first prior art is that the amount of a signal to be qualified is accumulated with the elongation of the complementary strand, resulting in difficult measurement of a change in the signal amount which corresponds to the incorporation of one base. Thus, it is difficult to determine a DNA base sequence having a large length (a large number of bases).

In the second prior art, all of the 4 kinds of the bases labeled with 4 kinds of fluorophores, respectively, are incorporated into a complementary strand, but this incorporation is technically difficult. As described hereinafter, fluorophores which emit a large amount of fluorescence and can be distinguished from one another by separation of the fluorescence into its spectral components have a large molecular size, so that owing to steric hindrance, it is difficult to incorporate a plurality of fluorophore-labeled nucleotides side by side into the same complementary strand. Another problem in the second prior art is that the release of the bases one by one by the use of endonuclease is difficult to control. When a plurality of bases are continuously released in a shorter time outside the detection limit, the bases released are detected at the same time, so that the order of the bases released, i.e., the base sequence cannot be determined. For determining the base sequence, the release of the bases should be intermittent, not continuous, but such control is difficult.

In the third prior art, the MdNTPs not incorporated into the template should be removed from the solution in the step of detecting the MdNTP incorporated into the template and the step of returning this MdNTP to its original state at which the elongation is possible, and MdNTPs should be added to the solution at the time of starting the next and new cycle. If these operations are neglected, a signal from the MdNTP incorporated into the template is mixed with that from the MdNTPs not incorporated into the template, so that the objective signal from the MdNTP incorporated into the template cannot be accurately measured. Moreover, if the protecting groups of the MdNTPs not incorporated into the template are also removed and the dNTPs produced by the removal of the protecting group are incorporated into the template, the progress of the predetermined cycle is blocked. Therefore, the composition of the solution should be changed at least twice per cycle, and this operation lowers the base sequence determination rate. Thus, there is the following problem: if even a small amount of the MdNTPs not incorporated into the template remain in the solution owing to the insufficient change of composition of the solution, they cause much noise in the measurement.

An object of the present invention is to provide method and apparatus for determining a very long DNA base sequence by determining one by one the kinds of the bases of nucleotides incorporated during the elongation reaction of a complementary strand using polymerase, in order to solve various problems in the proposed DNA sequencing methods using no electrophoresis.

In the present invention, a template DNA single molecule (a sample) is held in the field of view of a fluorescence microscope, a complementary strand is elongated by one base each time while controlling the elongation, and one fluorophore-labeled base incorporated thereinto is measured as a single molecule. To conduct DNA sequencing, it is sufficient that the kinds of the bases of nucleotides incorporated by the elongation reaction of the complementary strand using polymerase can be monitored one by one. All nucleotides to be incorporated are chemically modified so as to satisfy the following two conditions at the same time: (1) the elongation reaction does not proceed after the incorporation of one nucleotide, and (2) after the determination of the kind of the nucleotide incorporated, the incorporation of the next nucleotide is made possible. These two conditions can be fulfilled, for example, by combining caged compounds having fluorophores, respectively, as labels with nucleotides, respectively. The caged compound refers to a compound which masks the residue concerned in activity of a physiologically active substance with a nitrobenzyl group or the like and releases the modifying group on light irradiation. For example, the caged compound is a substance having a 2-nitrobenzyl group introduced thereinto which releases the 2-nitrobenzyl group on ultraviolet irradiation and is widely used in the field of biology (Annu. Rev. Biophys. Biophys. Chem. 18, 239–270 (1989)). Molecular Probes Inc. and the like sell various caged compounds. As shown in FIG. 1, the chemically modified nucleotides used in the present invention are caged compounds obtained by bonding a 2-nitrobenzyl group to a physiologically active substrate X (a nucleotide), and have the following capability: there is inhibited the inherent activity of the nucleotide without the chemical modification, i.e., the activity to undergo continuous incorporation by the synthetic reaction of a complementary strand, and the caged substance (2-nitrobenzyl group) is released by irradiation with ultraviolet light of 360 nm or less, whereby the chemically modified nucleotide can be converted to the substrate X or HX, which has its inherent physiological activity. In FIG. 1, R is H or an alkyl group (e.g. $CH_3$).

FIGS. 3 to 7 show a process for producing Texas Red-labeled caged dGTP as an example of the chemically modified nucleotide having the above-mentioned capability. In FIG. 3, a derivative of dGTP (FIG. 2) (Science 238, 336–341, 1987), a starting material for chemically modifying the base, is reacted with a water-soluble carbodiimide ($HOOC(CH_2)_2COOH$) to obtain a dGTP derivative having a carboxyl group as a linker end. On the other hand, as shown in FIG. 4, 2-nitroacetophenon (Aldrich, N920-9) is reacted with nitric acid to introduce a nitro group thereinto at the carbon 4 position, and the nitro group is reduced into an amino group. As shown in FIG. 5, the compound on the right side in FIG. 4 is reacted with Texas Red (Molecular Probes, T-353) to be bonded thereto. Next, as shown in FIG. 6, the compound on the right side in FIG. 5 is reacted with $NH_2$—$NH_2$ and then $MnO_2$ to convert the acetophenone group of the compound on the right side in FIG. 5 to a diazoethane group (J. Am. Chem. Soc. 110, 7170–7177, (1988)). The compound on the right side in FIG. 3 and that on the right side in FIG. 6 are reacted to obtain a fluorophore (Texas Red)-labeled caged nucleotide (dGTP), i.e., dGTP having as an introduced group a 2-nitrobenzyl group having Texas Red attached thereto as a label, as shown in FIG. 7. Also for other kinds of bases, fluorophore-labeled caged nucleotides (nucleotides having a fluorophore label-attached caged compound bonded thereto) can be synthesized.

It has been confirmed by various experiments that a substance labeled in the base portion of a nucleotide like the substance shown in FIG. 7 can be incorporated by the elongation reaction of a complementary strand using polymerase. For example, it has been confirmed that dideoxynucleotides ddNTPs labeled with various fluorophores, respectively, in their base portions, i.e., terminators for the synthesis of a complementary strand are incorporated by the synthesis of a complementary strand (Nucleic Acids Res. 20, 2471–2483 (1992)). In the case of fluorophores having a large molecular size, no continuous incorporation of two or more fluorophore-labeled deoxynucleotides occurs because of steric hindrance (Anal. Biochem. 234, 166–174 (1996)). That is, a deoxynucleotide labeled with a relatively large fluorophore as in FIG. 7 can be incorporated by the synthesis of a complementary strand but the complementary strand, is not further elongated after this incorporation. When the compound shown in FIG. 7 is irradiated with ultraviolet light of 360 nm or less, its chemical structure is changed as shown in FIG. 8 according to the photochemical reaction shown in FIG. 1, so that the caged substance having the fluorophore attached thereto is released from the base portion of the compound shown in FIG. 7. When the compound is subjected to the same reaction as above after being incorporated into the complementary strand, the steric hindrance is removed, so that the complementary strand is elongated again. In this case, the linker portion remains in the base as shown in FIG. 8 but it does not affect the elongation of the complementary strand because of its small size.

That is, when the elongation reaction of a complementary strand with polymerase is carried out by using as substrates, Texas Red-labeled caged dGTP shown in FIG. 7 and caged dATP, dCTP and dTTP which have been labeled with different fluorophores, respectively, the elongation reaction can be controlled so that the bases may be incorporated one by one as described above. Furthermore, the kinds of the bases incorporated can be determined by fluorescence measurement. The fluorescence measurement is carried out by conducting laser irradiation or the evanescent irradiation described hereinafter after spatially separating the incorporated nucleotide from other suspended nucleotides in order to excite only the incorporated nucleotide but not the other suspended nucleotides by irradiation with exciting laser beams. The base sequence of a template DNA can be determined by incorporating the fluorophore-labeled caged nucleotides one by one by reaction with polymerase by repeating the above steps, i.e., (1) the incorporation of one of the fluorophore-labeled caged nucleotides by the use of polymerase, (2) the excitation of the incorporated fluorophore label by laser irradiation, (3) the separation of the emitted fluorescence into its spectral components and the determination of the kind of the base from the kind of the fluorophore, and (4) the release of the fluorophore-labeled caged substance by the photochemical reaction caused by ultraviolet irradiation.

Next, there is explained below single-molecule measurement in which fluorescence from a fluorophore labeling one nucleotide incorporated is detected. FIG. 9 is a schematic diagram showing an outline of the structure of the principal part of an apparatus for carrying out the single-molecule measurement. Since impurities, dust and the like extremely interfere with the single-molecule measurement, all operations are carried out in a clean room and close attention is paid to all optical systems. A cell filled with a buffer solution is located over the objective lens of an inverted fluorescence microscope, and a sample DNA 7 as a template is held in the field of view of the fluorescence microscope in the buffer solution by the technique described hereinafter. The position of holding the sample DNA is in close vicinity to the inner top surface of the cell, and its distance from the top surface is maintained at 100 nm or less. A prism 4 is located on the outer top surface of the cell. Exciting laser beams 1 are introduced obliquely from above through the prism 4, perfectly reflected from the inner top surface of the cell, and then conducted obliquely upward through the prism 4. In this case, a slight amount of exciting light called evanescent waves 13 is infiltrated into the buffer solution in the cell in the vicinity of the top surface. The intensity of the exciting light decreases exponentially with an increase of the distance from the inner top surface of the cell. When Ar laser beams of 515 nm are used, the intensity becomes 1/e at a distance of about 150 nm from the top surface. The above irradiation method is called an evanescent irradiation method. When the evanescent irradiation method is adopted, only a substance present at a distance of 150 nm or less from the inner surface of the cell is excited, and background light in fluorescence measurement, such as Raman scattering in water can be reduced to the utmost, so that a single molecule can be subjected to fluorescent measurement (Nature 374, 555–559 (1995)). The fluorescence emitted is monitored as a fluorescence-microscopic image by means of a high-sensitivity two-dimensional camera through the objective lens from under the cell. Since one fluorophore-labeled nucleotide (fluorophore-labeled caged nucleotide) 9 incorporated by polymerase reaction 10 starting from a primer 8 is fixed on the template DNA 7, the fluorescence is observed as a bright spot in a two-dimensional image.

On the other hand, since non-incorporated, suspended, fluorophore-labeled nucleotides move about in the cell actively and three-dimensionally owing to Brownian motion, each of the fluorophores is not observed as a bright spot in the two-dimensional image but causes an increase of the whole background light. However, since the space where the fluorophores are excited extends to only 150 nm or less from the inner surface of the cell, the increment of the background light is so small that the single-molecule measurement of the fluorophore fixed on the template DNA can be carried out. The two-dimensional image is divided in four by a prism located on a light-receiving optical system and passed through different filters to be detected, and the kind of the fluorophore is determined in a moment, whereby the kind of base of the incorporated nucleotide is determined. This fluorescence selection method is described in detail in JP-A-2-269936. The evanescent irradiation method is adopted in the same manner as above also for releasing the fluorophore-labeled caged substance of the incorporated nucleotide 9. Ultraviolet pulse laser beams 2 are introduced obliquely from above through the prism 4, perfectly reflected from the top surface of the cell, and then conducted obliquely upward through the prism 4. The space extending to 150 nm or less from the inner surface of the cell is irradiated with ultraviolet light, and the fluorophore-labeled caged substance of the incorporated nucleotide is selectively released. In this case, there is a possibility that the fluorophore-labeled caged substances of a very small number of suspended nucleotides accidentally present in the space extending to 150 nm or less from the inner surface of the cell may also be released and that the resulting chemically non-modified nucleotides may be incorporated by the subsequent polymerase reaction. For eliminating this possibility, the buffer solution in the cell is always allowed to flow in one direction so that fresh buffer solution may be supplied.

Next, there is explained below a structure for holding a single molecule of the template DNA 7 in the field of view of the fluorescence microscope. Beads (solid carriers) 5 and 6 with a diameter of about 100 nm are attached to the ends, respectively, of the sample DNA 7 which is used as a template. As to a material for the beads, the beads are made of polystyrene, and the bead 6 is magnetic. The sample DNA 7 is introduced into the buffer solution in the cell, and the nonmagnetic bead 5 attached to the single DNA molecule is captured in the field of view of the microscope in the cell by the use of a laser trap 3 (Science 271, 795–799 (1996)). optical tweezers using a laser as a typical light source is a technique which is recently rapidly spreading as a non-contact manipulator (Optics Lett. 11, 288–290 (1986)). In particular, a laser trap using an IR laser is widely utilized because the influence of irradiation is minimum when a sample derived from a living body sample is used (JP-A-2-91545). When laser beams are condensed in water with a lens, fine particles in water can be captured in the vicinity of the focus of the lens with a restrainting force of approximately 2–6 pN/mW. After completion of the laser trap for the bead (solid carrier) 5 on one side of the single sample DNA 7, a magnetic field is applied in a direction parallel to the top and under surfaces of the cell to allow the magnetic bead 6 on the other side to generate a static magnetic force 11, whereby the single DNA molecule 7 is extended (Science 271, 1835–1837 (1996)). The extending force is controlled by varying the intensity of the magnetic field. While maintaining the above state, the stage of the microscope which has the cell fixed thereon is slowly lowered and it is brought to a position 100 nm or less under the inner top surface of the cell while capturing the single DNA molecule 7.

As explained above, in the present invention, base sequence determination can be carried out by using one kind of sample DNA, and the base sequence of the sample DNA can be determined with only complementary strand synthesis by using polymerase reaction. No trouble is caused in the measurement even if a polymerase molecule catalyzing the elongation of the complementary strand releases from DNA molecule and another polymerase molecule continues the elongation of the complementary strand. That is, a base sequence having a substantially desirable length can be determined by successively supplying active polymerase molecules. In the present invention, the repeated solution replacement, the problem in the first prior art, is not necessary. Furthermore, in the present invention, since the fluorophore incorporated into the complementary strand is released every cycle, there is no problem of accumulation of the amount of a signal from the fluorophore, so that base sequence determination can be carried out irrespective of the length (number of bases) of DNA. On the other hand, the incorporation of fluorophores in succession into a complementary strand, the problem in the second prior art, is not necessary in the present invention. In the second prior art, it is difficult to control the release of bases one by one and the elongation by controlling the activities of the enzymes. By contrast, in the present invention, the elongation is structurally controlled, so that the elongation can be controlled for each base without controlling the activity of the enzyme. In addition, the change of the composition of the solution, the problem in the third prior art, is not necessary in the present invention. That is, in the present invention, only a chemically modified nucleotide incorporated into a template can be selectively measured in the presence of chemically modified nucleotides not incorporated into the template, and the chemically modifying substance can be released selectively only from the nucleotide incorporated into the template. Therefore, the chemically modified nucleotides not incorporated into the template need not be removed from the solution during the cycle.

The rate of the base sequence determination according to the present invention is dependent on the cycle time of the steps explained above. The step of incorporating a molecule of fluorophore-labeled caged nucleotide with polymerase can be carried out in 0.1 second or less. Various kinds of DNA polymerases are on the market and permit incorporation of nucleotides at a rate of 30 bases per second in the case of the slowest elongation rate. That is, the average time required for the incorporation of one base is 0.03 second and the above time of 0.1 second is a considerably high estimate. 0.5 second is required for carrying out the steps of exciting the incorporated caged nucleotide by laser irradiation, separating the emitted fluorescence into its spectral components, and determining the kind of the base from the kind of the fluorophore.

For the single-molecule fluorescence measurement, a television rate, i.e., an exposure time of 0.03 second or less may be employed (Nature 374, 555–559 (1995)), though in the present invention an exposure time of 0.5 second is employed for high-sensitivity measurement. The laser irradiation time is also 0.5 second and the laser irradiation is synchronized with fluorescence exposure. The determination of kind of the base from the kind of the fluorophore is completed in 0.1 second or less, and it does not affect the cycle time because it can be carried out simultaneously with the subsequent step. The step of releasing the fluorophore-labeled caged substance by ultraviolet irradiation can be completed in 0.1 second or less. The fluorophore-labeled caged substance can be released in the order of millisecond by ultraviolet pulse laser irradiation for 10 nanosecond (Annu. Rev. Biophys. Biophys. Chem. 18, 239–270 (1989)). When the steps described above are automatically repeated by using a computer, the cycle can be repeated once in 1 second even if the time required for controlling a laser and a camera is assumed to be 0.3 second per cycle. Since the kind of one base can be determined per cycle, the rate of the base sequence determination becomes one base per second or shorter. When the method of the present invention is applied to the determination of the base sequence with a length of 1 M bases of a YAC clone, a typical large clone, the determination can be completed in 1 M seconds, i.e., about 12 days which is 1 order of magnitude shorter than a time required for carrying out the determination by a conventional method. According to the method of the present invention, a plurality of sample DNAs can be dealt with in parallel by holding them in the same field of view of a microscope. The base sequences in different regions of one and the same DNA sample can be determined at the same time. For example, the double strand of the aforesaid sample DNA having a length of 1 M bases is separated, and the resulting two strands are fixed at positions, respectively, in the field of view of the microscope at which they can be independently measured. When the base sequences of the two strands are independently determined, the sample DNA is decoded from both sides, whereby the whole base sequence of the sample can be determined at a rate twice that described above. That is, the base sequence of a single molecule having a length of 1 M bases can be determined in only 6 days, so that very efficient genome analysis and genetic diagnosis are possible.

BRIEF DESCRIPTION OF THE DRAWINGS

FIG. 2, FIG. 3, FIG. 4, FIG. 5, FIG. 6 and FIG. 7 are schemes showing chemical reactions for a GTP derivative, a starting material for preparing the chemically modified nucleotide used in the present invention.

BEST MODE FOR CARRYING OUT THE INVENTION

Figure 1:
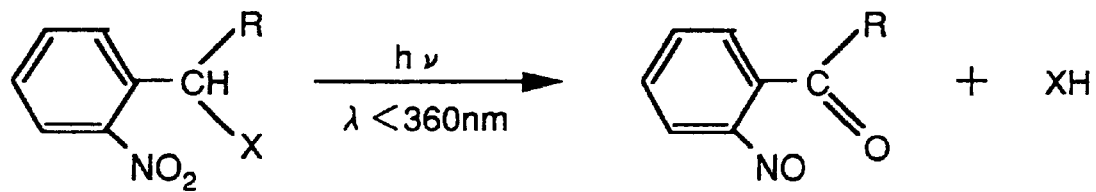
FIG. 1 is a scheme showing the photochemical reaction by ultraviolet irradiation of the caged compound used in the present invention.
Figure 2:
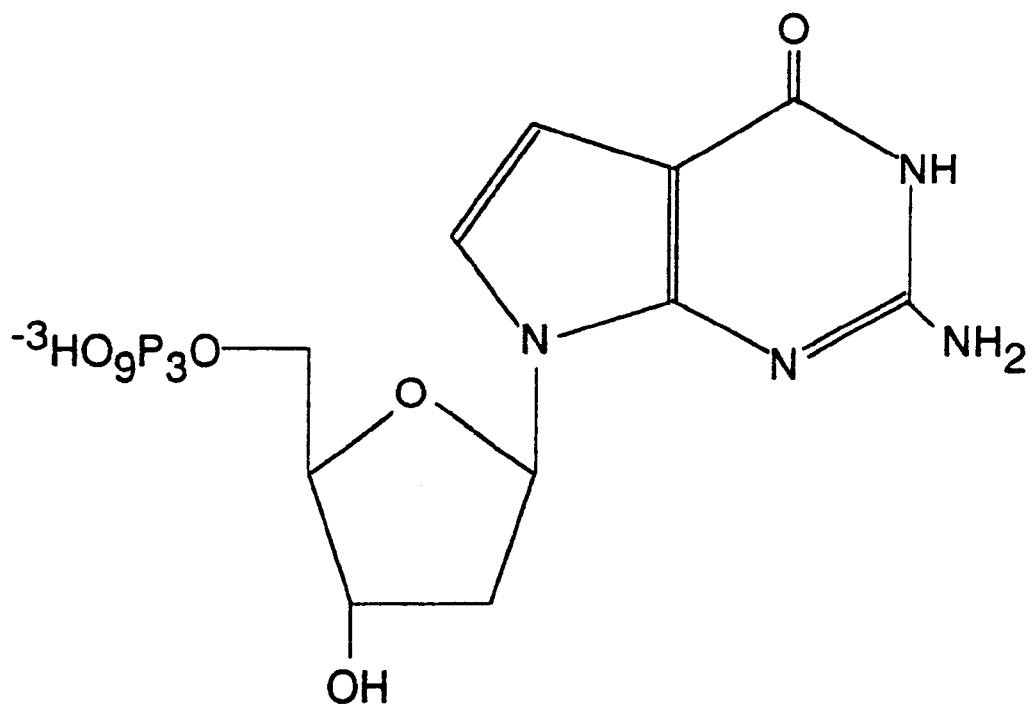
Figure 6:
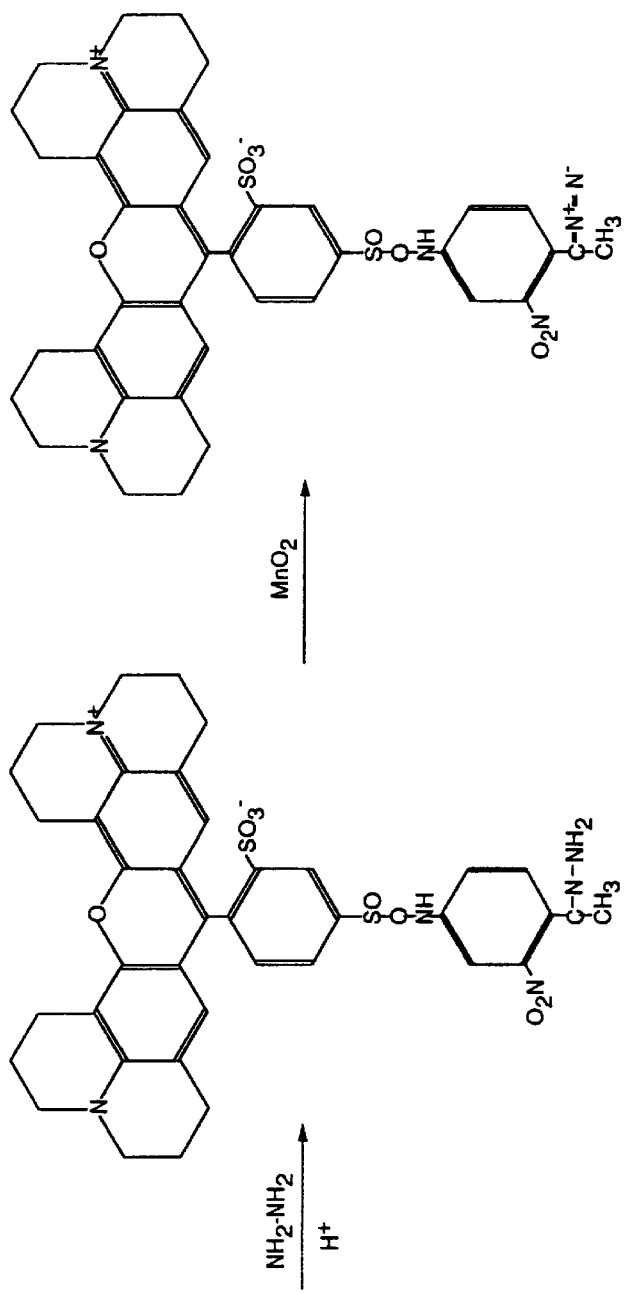
Figure 7:
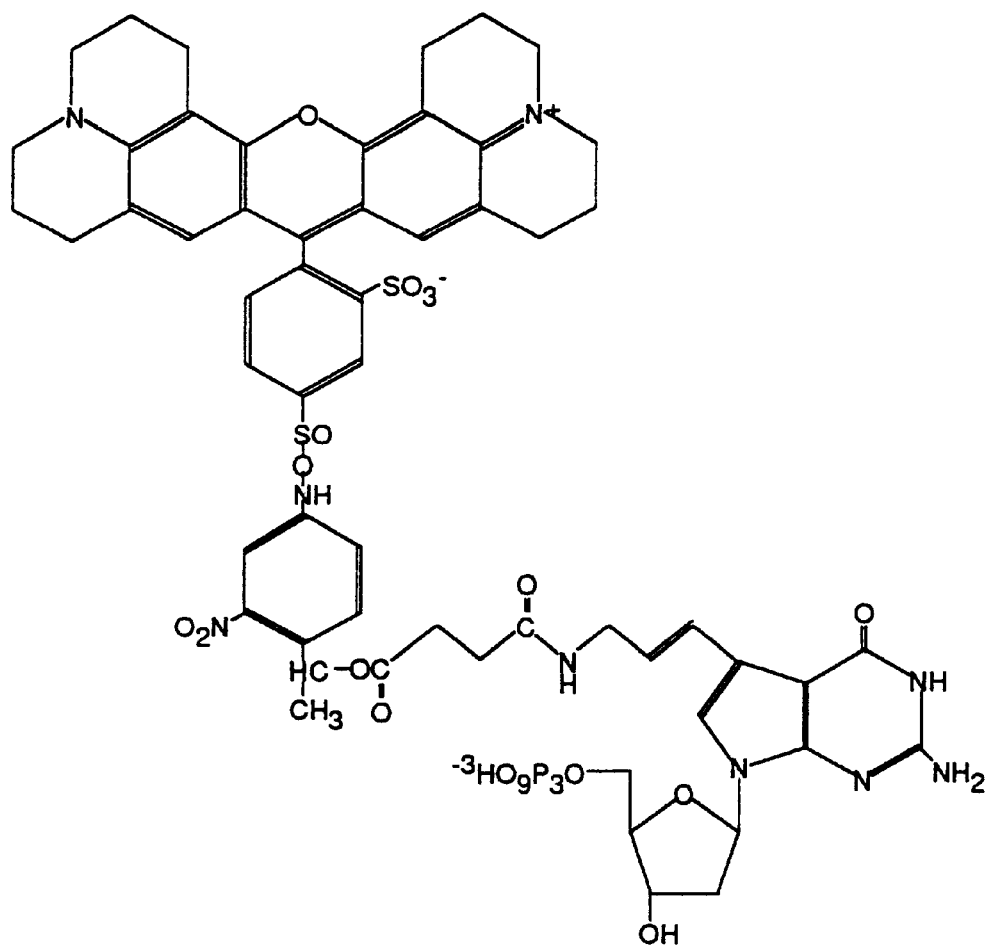

In order to explain the present invention in detail, it is explained below with reference to the attached drawings.

EXAMPLE 1

All operations are carried out in a clean room of class 1000 in order to prevent contamination of optical systems or a sample solution with impurities such as dust. The structure of the whole of an apparatus used in the present example is explained with reference to FIG. 10. As a microscope, an inverted phase-contrast and incident-light fluorescence microscope (IMT2-RFC, mfd. by Olympus Co., Ltd.) is used. This microscope makes it possible to observe an object by switching a phase-contrast image and a fluorescence image over to each other while fixing the field of view. As an objective lens 27, an oil-immersed 100-power lens (Plan·Apochromat×100, 1.40 NA, mfd. by Olympus Co., Ltd.) is used. In this case, as to the size of the field of view, the diameter is about 100 $\mu$m. A cell 25 equipped with a temperature-controlling function is set on the stage 26 over the objective lens 27. FIG. 11 shows the structure of the cell. The top surface 37 of the cell is made of a vitreous-silica slide glass of 1 mm thick, the under surface 38 of the cell is made of a vitreous-silica cover glass of 0.1 mm, and the distance between the two glass plates is 0.2 mm. Capillaries 39 and 40 are connected to the right and left ends, respectively, of the cell, and a solution is introduced into the cell through the capillary 39 and discharged through the other capillary 40. The flow rate of the solution in the cell is controlled with a pump. As the pump, one utilizing gravity head is used in order to prevent a pulsating flow. A Peltier element is connected to a portion excluding the vicinity of the field of view of the microscope of each of the top and under surfaces of the cell, whereby the temperature of the whole cell is made controllable in a range of 0° C. to 100° C. The objective lens 27 is brought into contact with the outer under surface 38 of the cell through a non-fluorescent oil incapable of emitting fluorescence on light irradiation. An electromagnet is located on the right of the cell 25 on the stage 26 shown in FIG. 10 and a magnetic field is generated horizontally in the cell so that a magnetic material in the cell may receive electrostatic magnetic force in the direction of the right of the cell.

Figure 10:
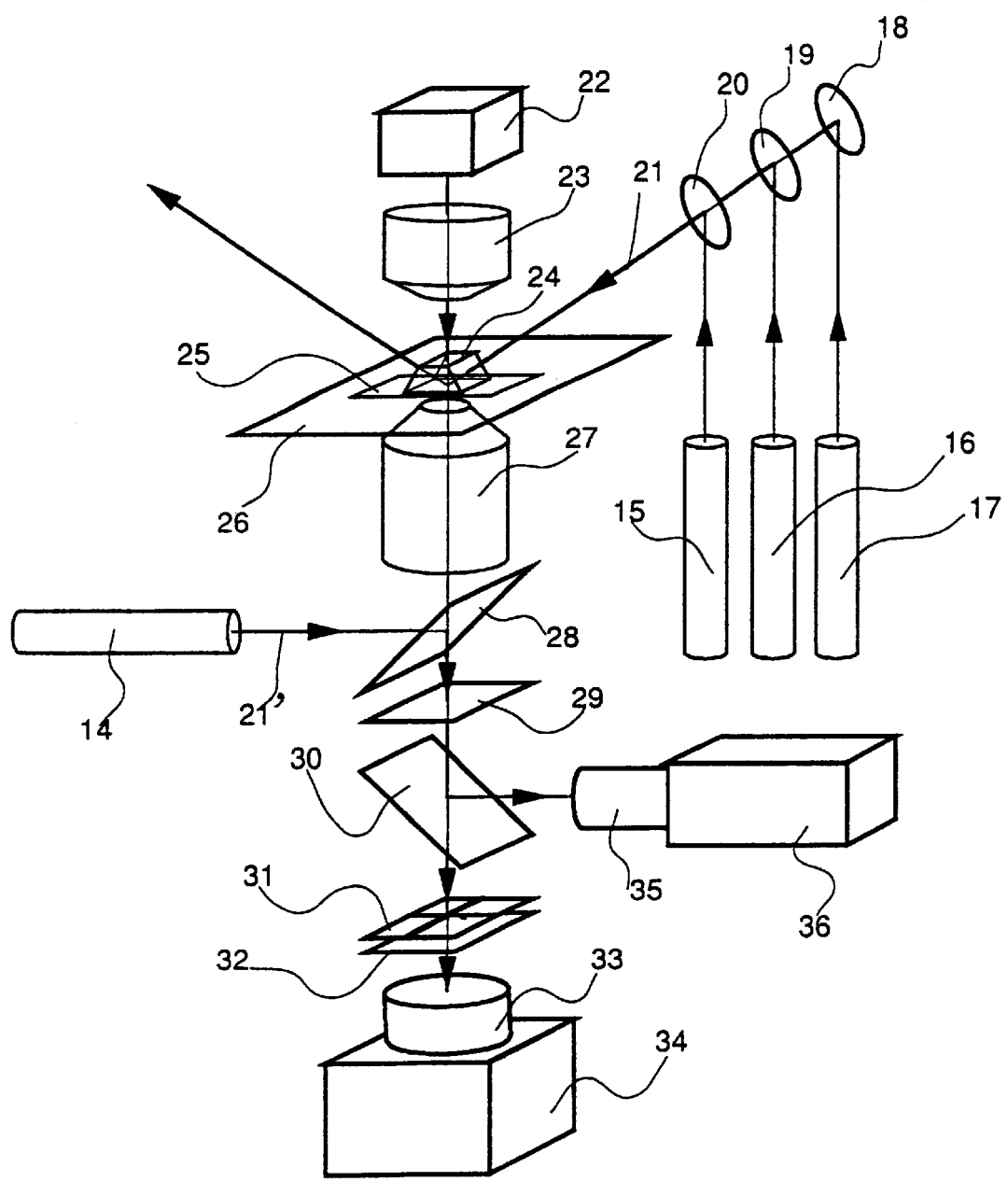
FIG. 10 is a schematic diagram showing an outline of the structure of a measuring apparatus used in the example of the present invention.
Figure 11:
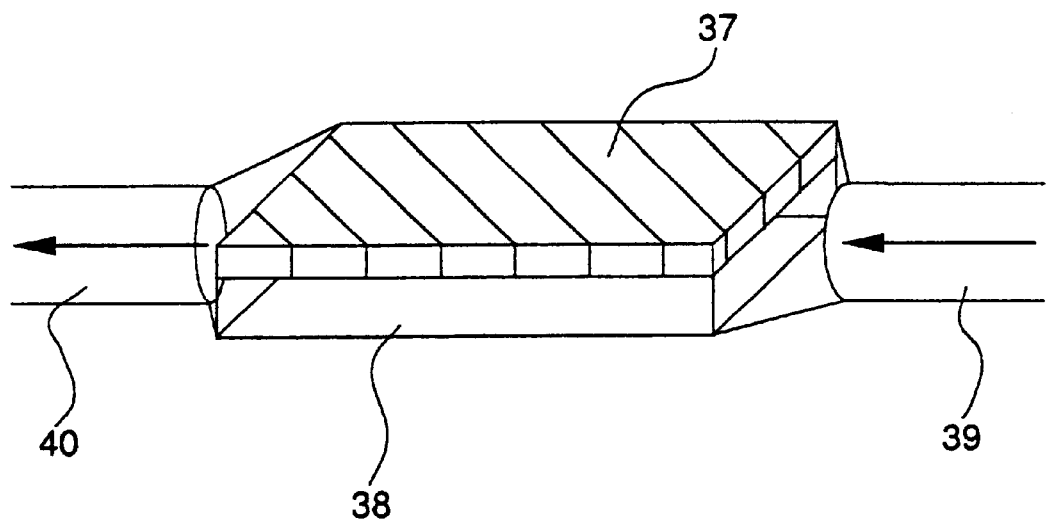
FIG. 11 is a schematic diagram showing the structure of a cell used in the example of the present invention.
Figure 12:
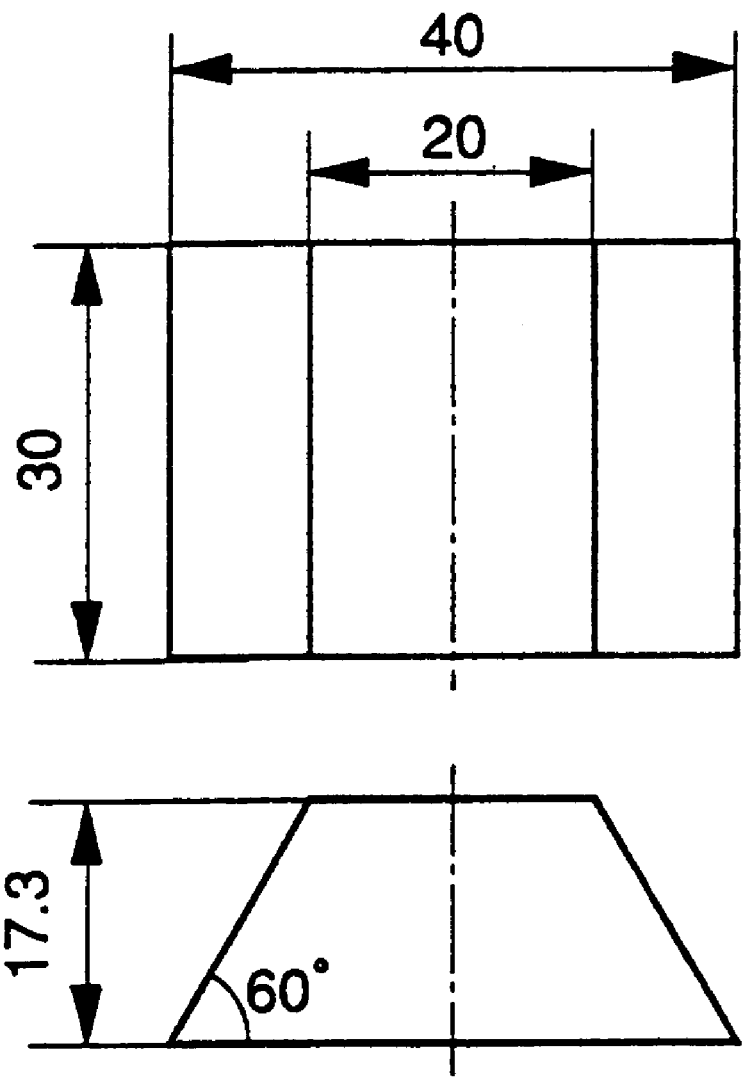
FIG. 12 is a diagram showing the structure of a prism used in the example of the present invention.

As shown in FIG. 10, a quartz prism 24 having an inclination of 60° is brought into contact with the outer top surface 37 of the cell through a non-fluorescent glycerol incapable of emitting fluorescence on light irradiation. FIG. 12 shows the shape of the prism 24. From just above the stage 26, light from a halogen lamp 22 for observing a phase-contrast image is condensed by a condenser lens 23 and introduced into the cell through the flat portion of the top surface of the prism 24. Laser beams of 488 nm from an Ar ion laser 15 (20 mW), laser beams of 532 nm from a YAG laser 16 (20 mW) and laser beams of 355 nm from a pulse oscillation YAG laser 17 (10 mJ) are cast on the cell 25 obliquely from above at an incidence angle of 68° with the stage 26 through the right slope of the prism 24 shown in FIG. 10, to be perfectly reflected from the internal surface of the cell. These three kinds of laser beams are made into coaxial beams 21 by means of a perfectly reflecting mirror 18 and dichromic mirrors 19 and 20, condensed to a diameter of about 100 $\mu$m with a lens having a focal length of 100 mm, and then reflected at the field of view of the microscope. The perfectly reflected laser beams 21 are allowed to emerge above at an angle with respect to the stage 26 through the left slope of the prism 24 shown in FIG. 10. On the other hand, laser beams of 1064 nm from a YAG laser 14 (100 mW) is reflected from a dichromic mirror 28, passed through the objective lens 27 to be condensed, and then introduced into the cell. The laser beams 21' is condensed to a diameter of about 1 $\mu$m or less with the objective lens 27, and the focus is set in the cell in the field of view of the microscope. The dichromic mirror is designed to reflect infrared rays selectively in incident light of 45°. The output, oscillation and casting on or introduction into the cell 25 of the light from the halogen lamp 22 and the laser beams from the 4 kinds of the lasers 14, 15, 16 and 17 are controlled by means of a computer.

Fluorescence emitted in the field of view of the microscope is made into a substantially parallel luminous flux by the objective lens 27 and transmitted by the dichromic mirror 28 and an infrared cut filter 29, and its light path is splitted in two directions by a beam splitter 30. The beam splitter 30 can be used as a half-mirror, perfectly reflecting mirror or non-mirror by freely switching them over to one another, and can distribute light in a predetermined proportion of 0% to 100%. The infrared cut filter 29 is set for perfectly cutting light of 1064 nm which cannot be completely removed by the dichromic mirror 28. The light path in the direction of reflection from the beam splitter 30 is subjected to image formation by a 2.5-power photographing lens 35 (NFK×2.5, mfd. by Olympus Co., Ltd.) and two-dimensionally detected in a video-rate CCD camera 36. This CCD camera is used mainly for capturing a sample DNA. Video signals can be observed in real time at video rate with a monitor. The detection plane of the CCD camera has an area of 12.8×12.8 mm and is composed of 512×512 aligned picture elements each having an area of 25×25 $\mu$m. Since the image magnification on the image formation plane is 100× 2.5=250 times, the area of the field of view is 51.2×51.2 $\mu$m and each picture element corresponds to 0.1×0.1 $\mu$m. On the other hand, light directed downward with respect to the objective lens 27 is transmitted by an optical element composed of a combination of a dividing-in-four prism 31 and 4 kinds of interference filters, subjected to image formation by a 2.5-power photographing lens 33 (NFK×2.5, mfd. by Olympus Co., Ltd.) and then two-dimensionally detected in a cooled two-dimensional CCD camera 34. The cooled two-dimensional CCD camera 34 is used mainly for fluorescence measurement. The detection plane of the cooled two-dimensional CCD camera has an area of 25.6× 25.6 mm and is composed of 1024×1024 aligned picture elements each having an area of 25×25 μm. Since the image magnification on the image formation plane is 100 ×2.5=250 times, each picture element corresponds to 0.1 ×0.1 μm.

Figure 13:
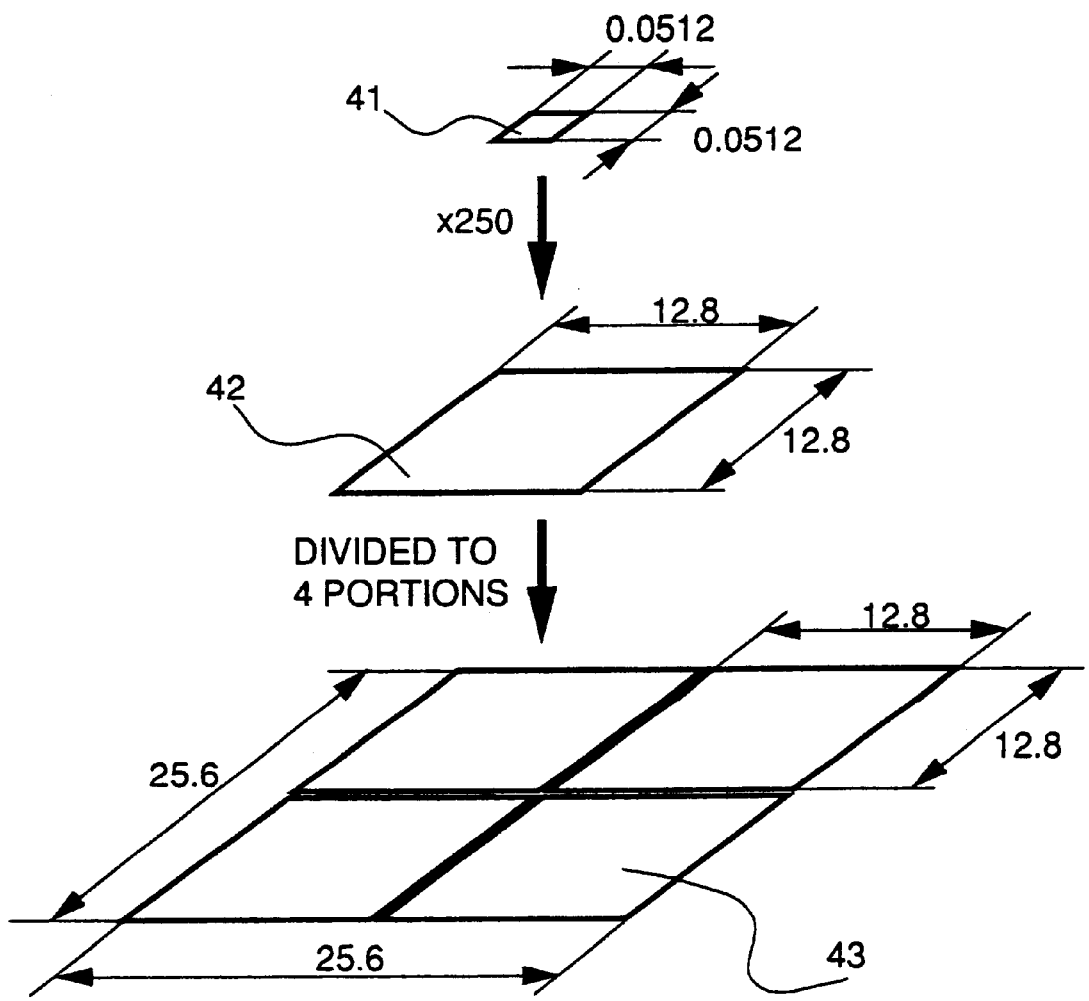
FIG. 13 is a diagram showing the field of view of a microscope used in the example of the present invention and an image formation plane to be divided in four.
Figure 14:
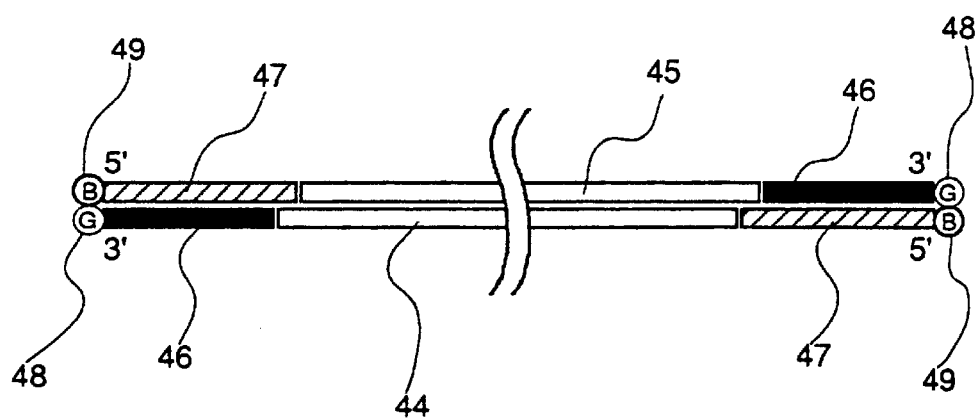
FIG. 14 is a diagram showing the structure of a sample DNA having oligonucleotides introduced into each end which is used in the example of the present invention.

As shown in FIG. 13, an image 41 in the field of view of 51.2×51.2 μm is divided in four by the dividing-in-four prism 31 inserted into the light path. As to the size of each of the images obtained by the division, each of them corresponds to an image 42 having an area of 12.8×12.8 mm on the detection plane. The image formation is carried out to obtain an image 43 having an area of 25.6×25.6 mm so that the four images may not overlap with one another. The interference filters corresponding to the four images have a transmission band with a transmittance of 70% or more in wavelength ranges of 500 to 520 nm, 540 to 560 nm, 560 to 580 nm, and 580 to 600 nm, respectively, and their transmittance outside the transmission band is $10^{-4}$ or less in a wavelength range of 300 to 1100 nm. Their transmittance at 355 nm, 488 nm and 532 nm, and the wavelengths of the laser beams are $10^{-6}$ or less. Fluorescence emitted from one spot in the field of view of the microscope is projected on the detection plane of the cooled CCD camera as 4 divided spots, and a pair of coordinates are assigned to each of the resulting 4 image spots. Therefore, of a plurality of bright spots on the 1024×1024 picture elements, only luminance informations concerning each of 4 bright spots, respectively, can be selectively transferred to a computer. The 4 spots are transmitted by the above-mentioned 4 kinds of the different interference filters, respectively, to be detected, and the ratio among the fluorescence intensities of the spots varies depending on the kind of the fluorophore which has emitted fluorescence. The kind of the fluorophore which has emitted fluorescence can be determined by measuring the ratio among the fluorescence intensities of the 4 spots. The example is explained below with reference to an actual measuring procedure. The whole base sequence of λDNA as a model example is determined. Since λDNA has a length of 48502 bases and the whole base sequence thereof is known, λDNA is the most suitable as a sample for confirming the principle of the method of the present invention. λDNA is obtained in the form of a straight double strand. A double-stranded oligonucleotide complementary to both ends of λDNA is synthesized and bonded to each end by ligase reaction. As shown in FIG. 14, in the synthetic double-stranded oligonucleotide, biotin 49 is attached as a label to the 5'-end of oligonucleotide 47 bonded to the 5'-end of each of the strands 44 and 45 of λDNA, and digoxin 48 is attached as a label to the 3'-end of oligonucleotide 46 bonded to the 3'-end of each of the strands 44 and 45 of λDNA. The base sequence of a portion not complementary to λDNA of the synthetic double-stranded oligonucleotide is composed of 20 bases or more and is used a priming site in the subsequent polymerase reaction.

Figure 15:
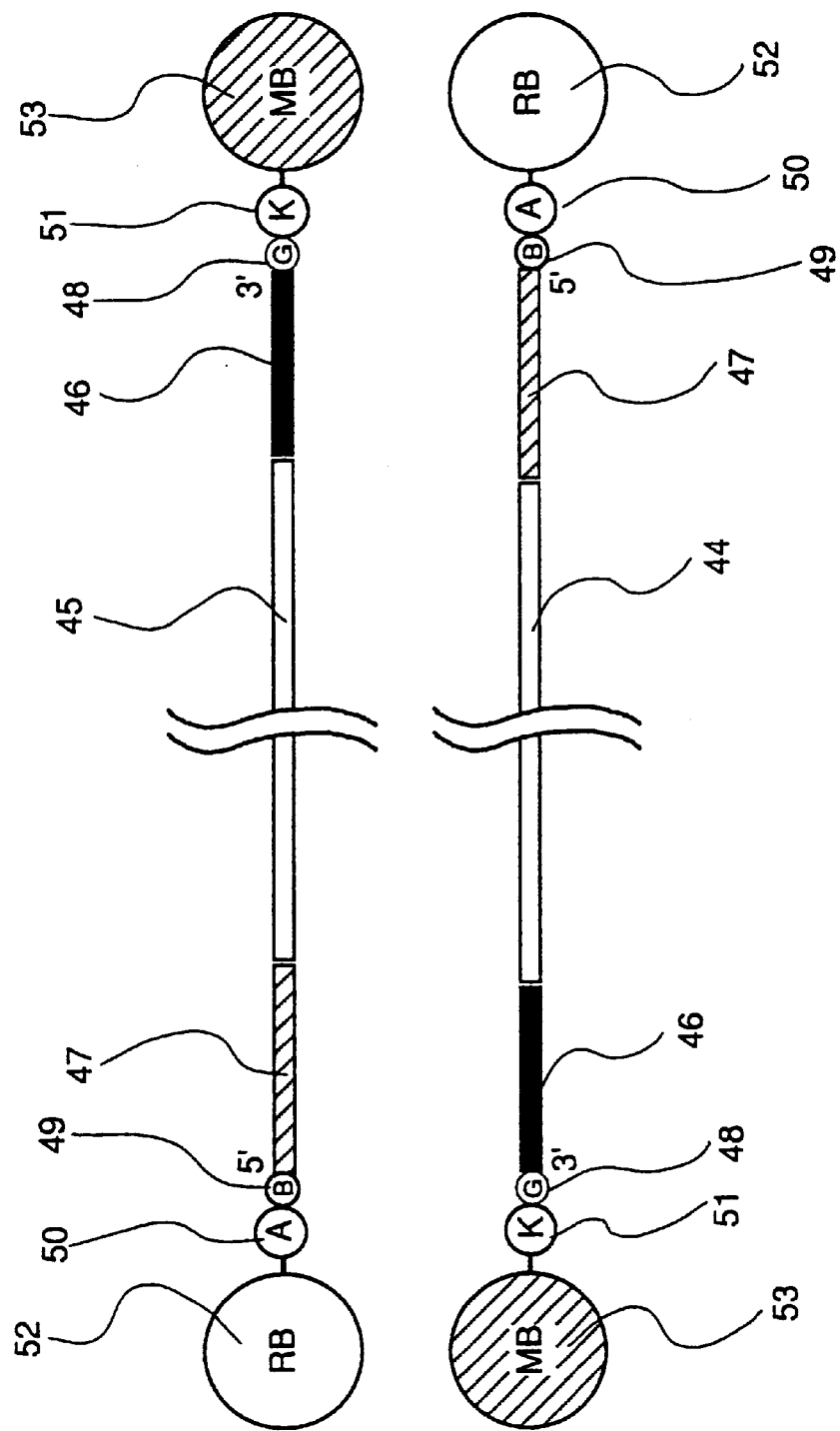
FIG. 15 is a diagram showing the structure of sample DNAs each having a bead (a solid carrier) and a magnetic bead (a solid carrier) attached to the ends, respectively, which are used in the example of the present invention.
Figure 16:
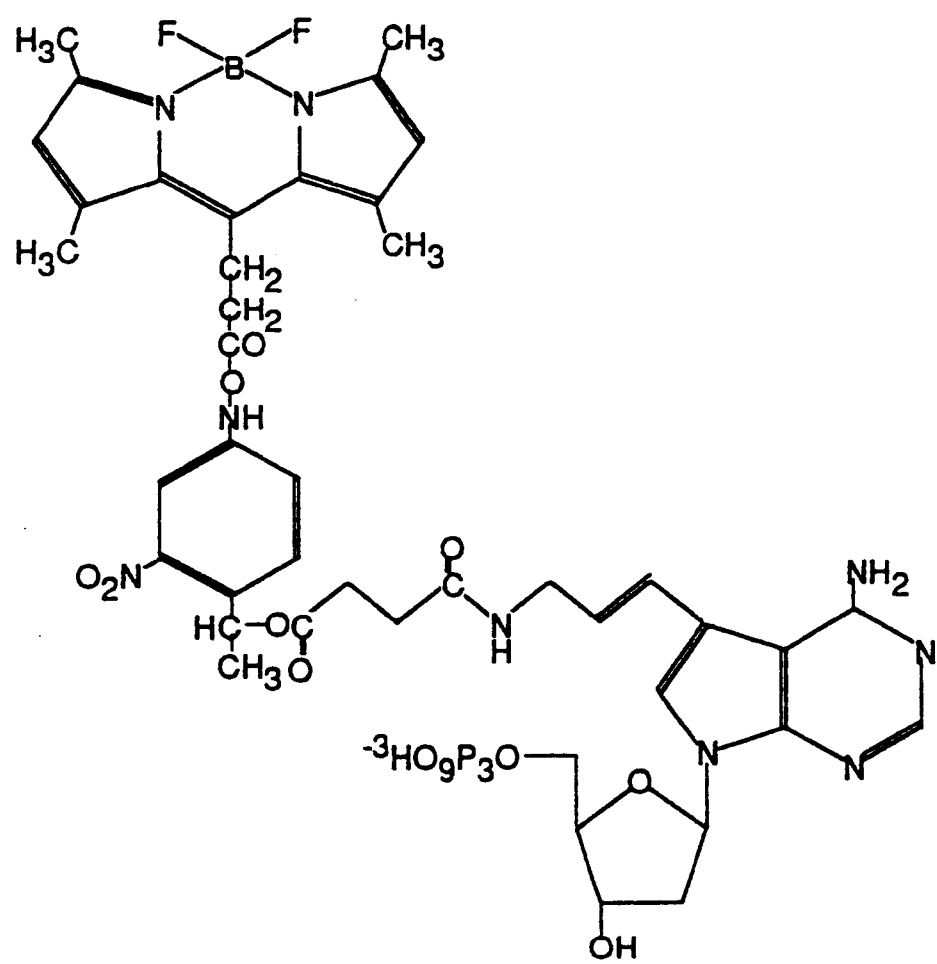
FIG. 16 is a diagram showing the structure of a BODIPY-labeled caged dATP used in the example of the present invention.
Figure 17:
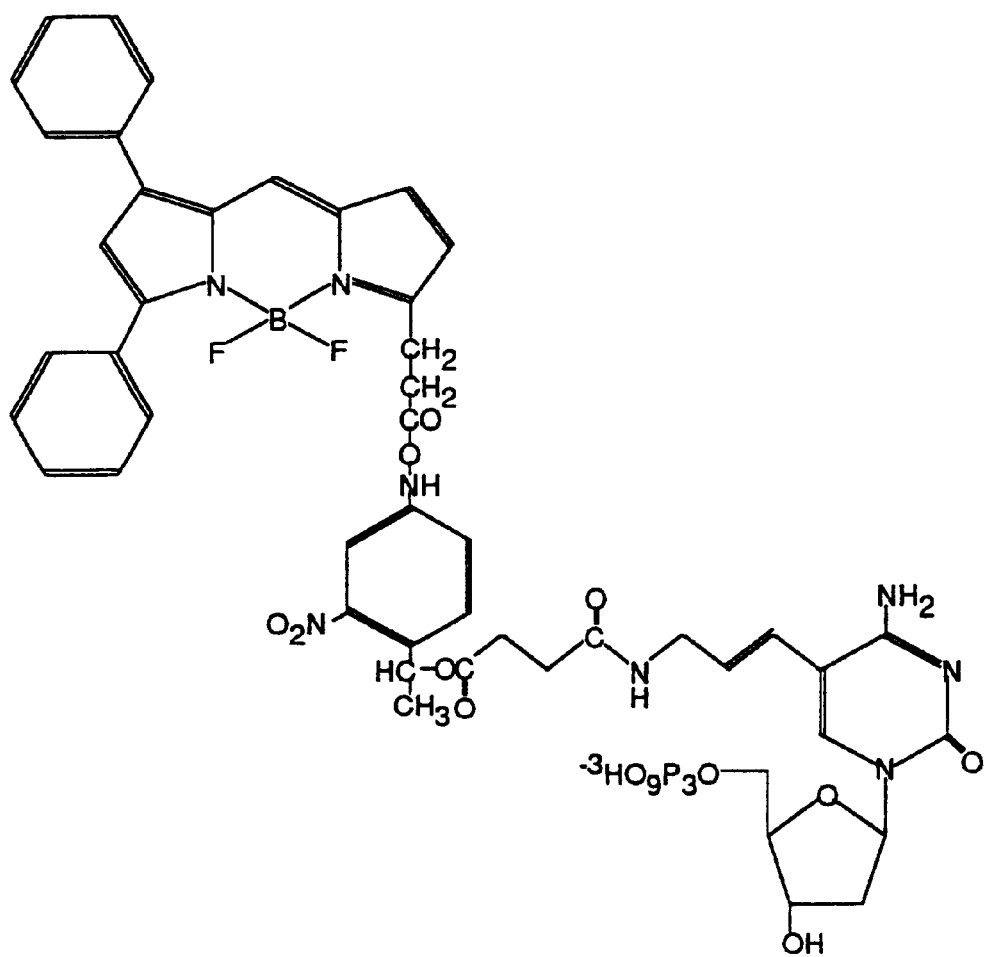
FIG. 17 is a diagram showing the structure of a BODIPY-labeled caged dCTP used in the example of the present invention.
Figure 18:
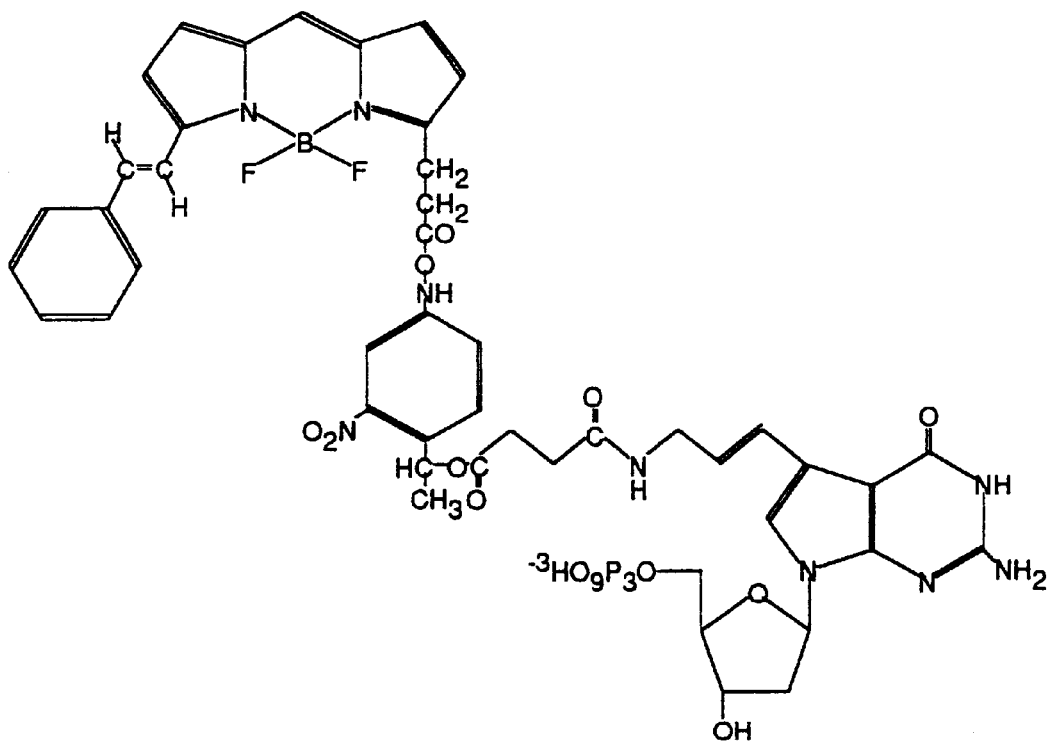
FIG. 18 is a diagram showing the structure of a BODIPY-labeled caged dGTP used in the example of the present invention.
Figure 19:
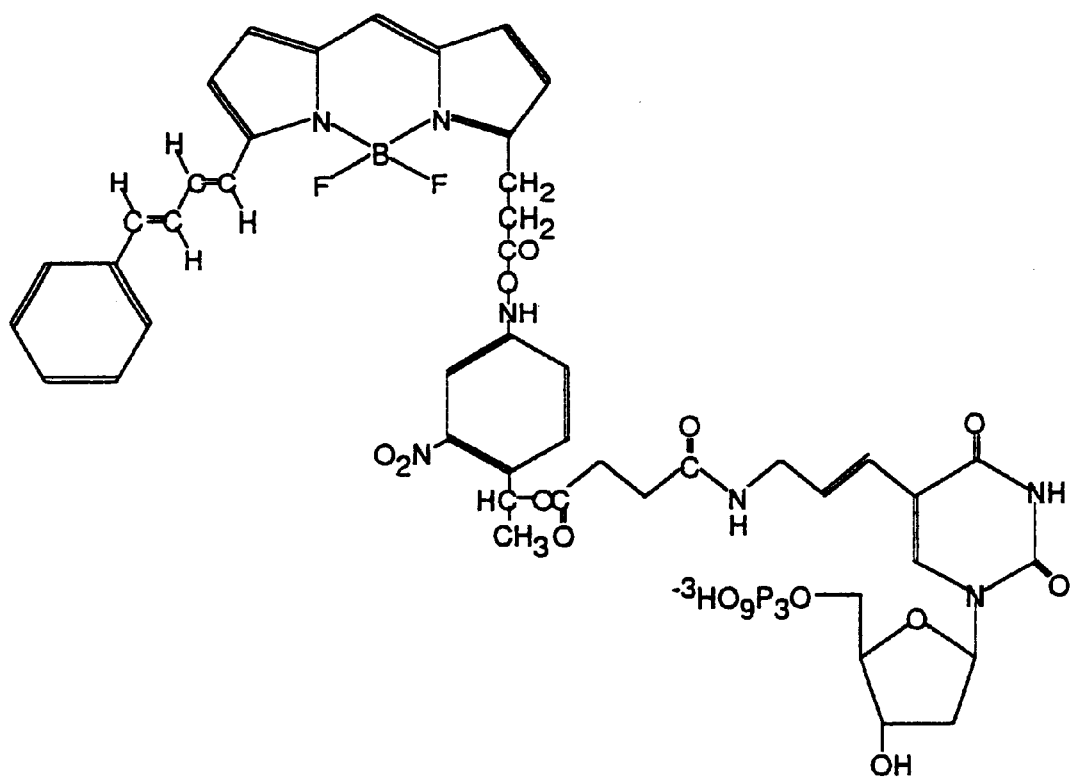
FIG. 19 is a diagram showing the structure of a BODIPY-labeled caged dTTP used in the example of the present invention.

On the other hand, as shown in FIG. 15, streptavidin 50 is attached to the outer surface of each polystyrene bead (a solid carrier) 52 with a diameter of about 0.1 μm by acid amide linkage. Anti-digoxin antibody 51 is attached to the outer surface of each magnetic polystyrene bead (a solid carrier) 53 with a diameter of about 0.1 μm by acid amide linkage. The λDNA composed of the strands 44 and 45 subjected to the ligation is denatured to assume a single-stranded state, and the above-mentioned beads are added thereto. Since there occurs very specific combination with a high coupling constant between biotin 49 and streptavidin 50 and between digoxin 48 and the anti-digoxin antibody 51, the nonmagnetic bead 52 is attached to the 5'-end of each of the strands 44 and 45 of λDNA and the magnetic bead 53 is attached to the 3'-end. Four kinds of chemically modified nucleotides having the structures, respectively, shown in FIG. 16 to FIG. 19 are synthesized in the same manner as explained with reference to FIG. 3 to FIG. 7. FIG. 16 shows a caged dATP having BODIPY 493/503 C3 (D-2190, mfd. by Molecular Probes, Inc.) as a label. FIG. 17 shows a caged dCTP having BODIPY 530/550 C3 (D-2186, Molecular Probes, Inc.) as a label. FIG. 18 shows a caged dGTP having BODIPY 564/570 C3 (D-2221, Molecular Probes, Inc.) as a label. FIG. 19 shows a caged dTTP having BODIPY 581/591 C3 (D-2227, mfd. by Molecular Probes, Inc.) as a label. Impurities such as unmodified nucleotides are previously removed by using a column or the like.

Figure 20:
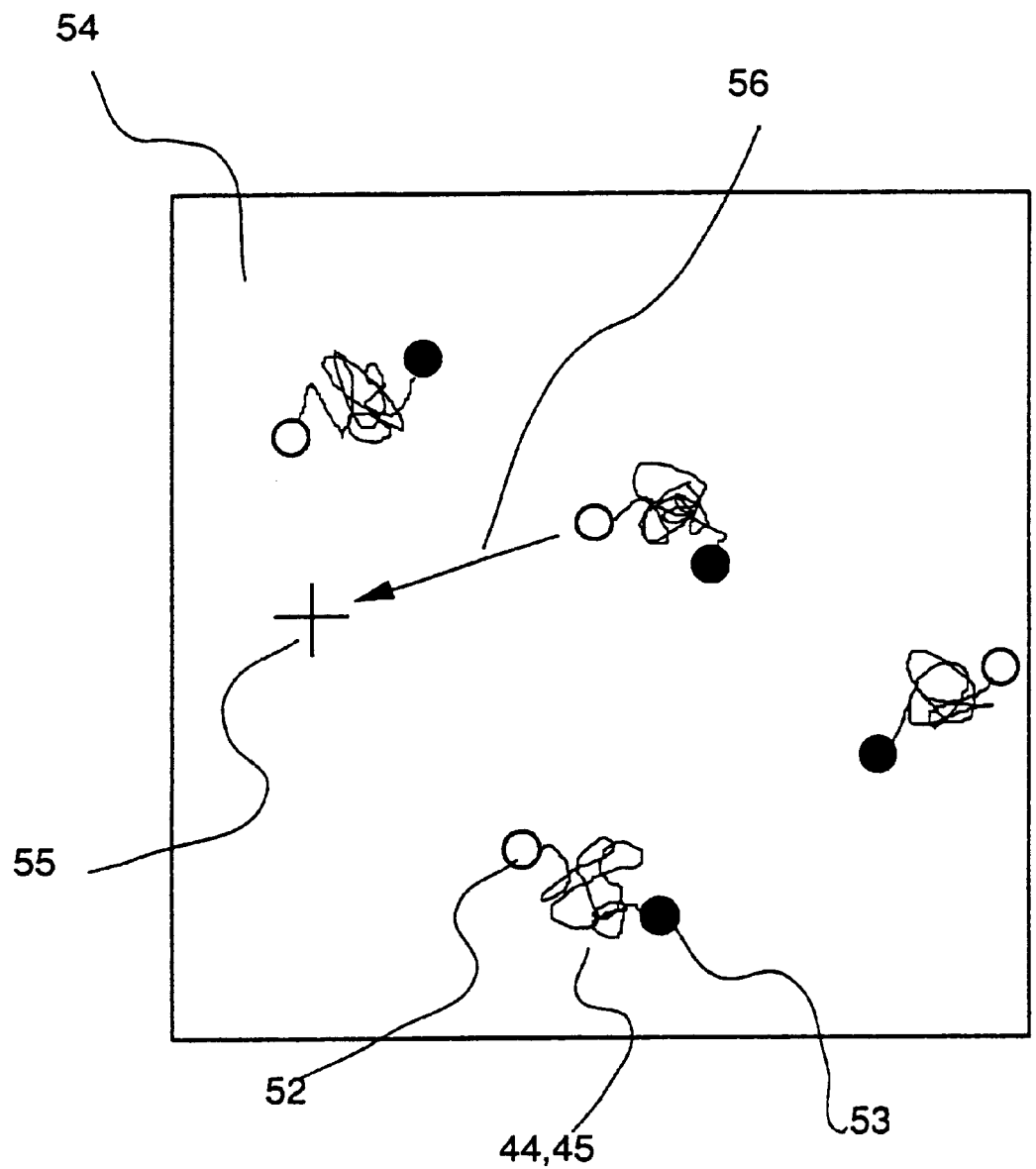
FIG. 20, FIG. 21, FIG. 22 and FIG. 23 are diagrams illustrating the fixation of the sample DNA in the field of view of a microscopic-image monitor.
Figure 21:
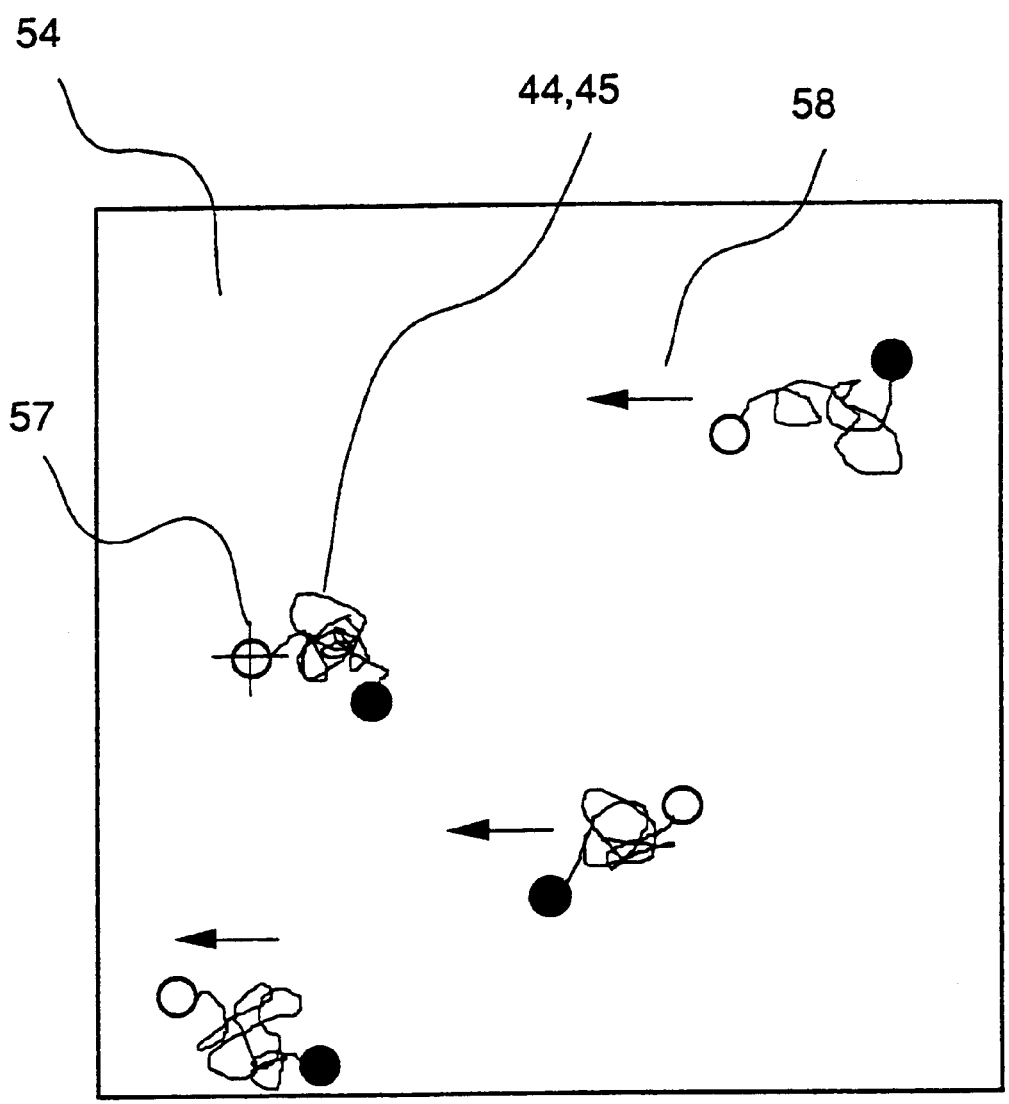
Figure 22:
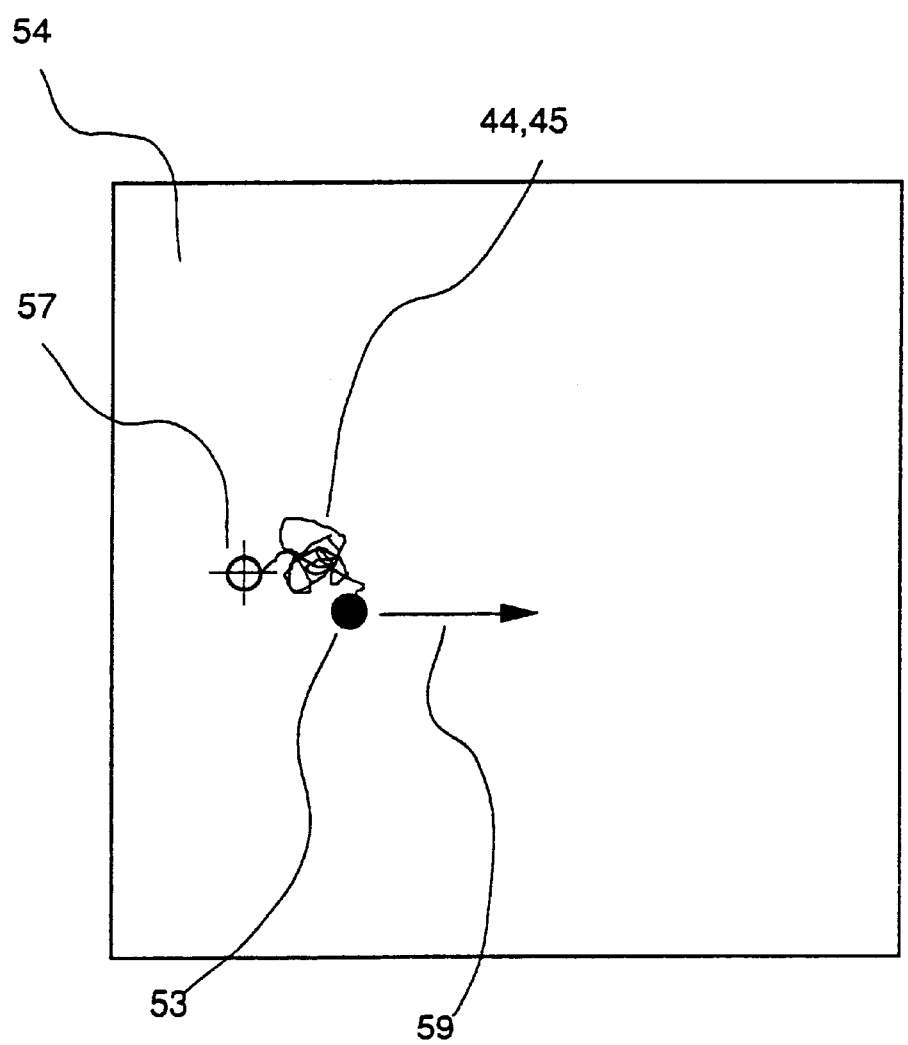
Figure 23:
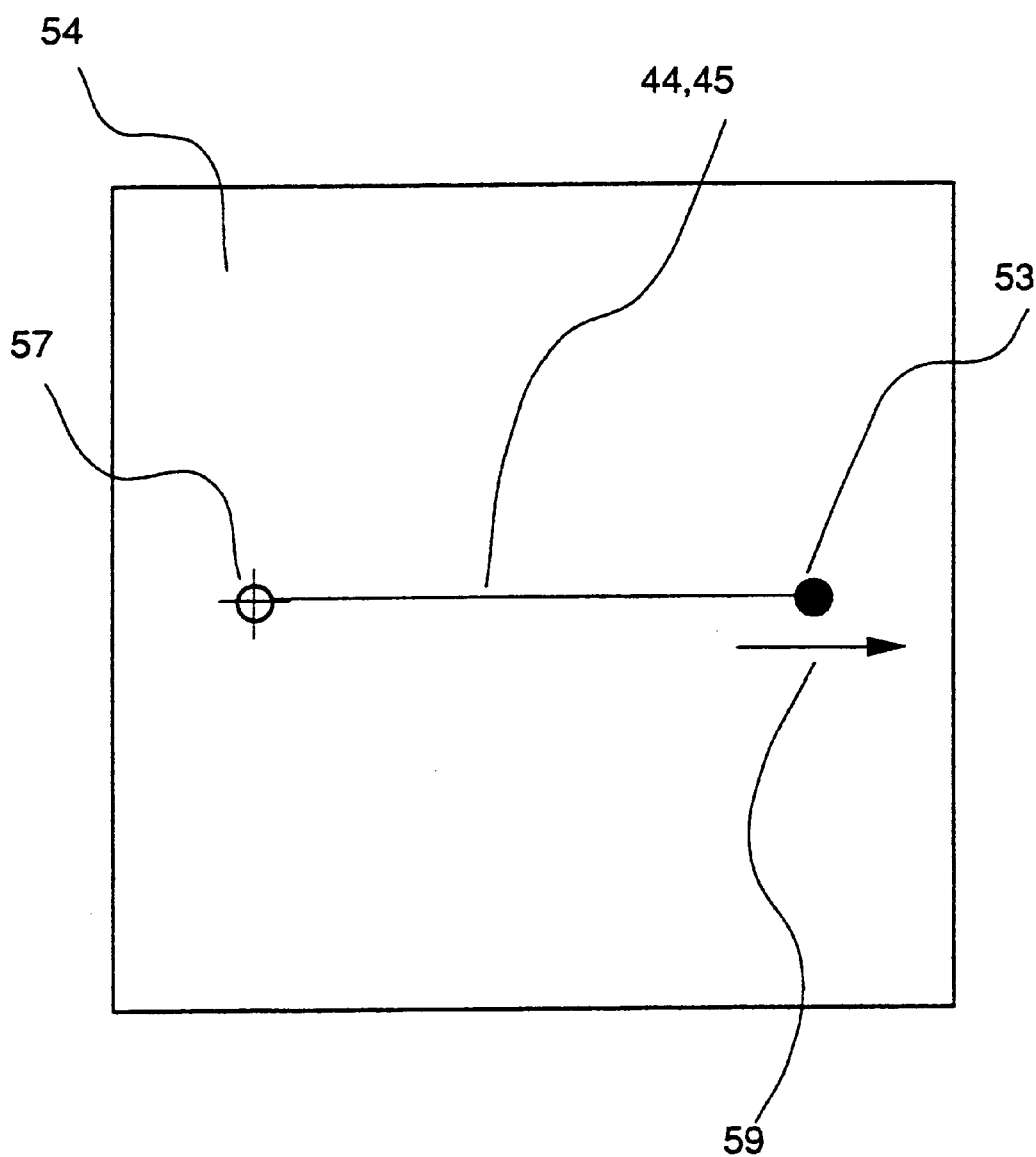

The strands 44 and 45 of λDNA each having the beads 52 and 53 attached to the ends, respectively are introduced each in the form of a single strand into the cell 25 fixed on the stage 26 of the microscope by allowing a buffer solution to flow. First, a phase-contrast microscope mode is adopted. The beam splitter 30 shown in FIG. 10 is made into a 100% reflecting mirror, and the field of view 54 shown in FIG. 20 to FIG. 23 is observed by means of a CCD camera 36 for capturing sample DNA and a video monitor by stopping the flow of the buffer solution. As shown in FIG. 20, the nonmagnetic bead 52 attached to the 5'-end of each of the strands 44 and 45 of the sample DNA is found on the monitor. The stage is horizontally moved (56) to place, as shown in FIG. 21, the aforesaid found bead 52 at a position 55 corresponding to a focus for infrared laser beams of 1064 nm which has been set at the middle on the left side on the monitor. Then, infrared laser beams of 1064 nm are oscillated and the above-mentioned found bead 52 is captured as a predetermined bead by means of a laser trap (57). Whether the capture has been achieved or not can be known at once by moving the stage. The buffer solution is allowed to flow again (58) to carry, as shown in FIG. 22, other non-captured beads and molecules of the single-stranded sample DNA out of the field of view. Subsequently, a magnetic field is horizontally generated by the use of an electromagnet to draw, as shown in FIG. 23, the magnetic bead 53 attached to the 3'-end of the strand of the sample DNA toward the right on the monitor (59), whereby the strand 44 or 45 of the sample DNA held between the beads attached to the ends of the strand are extended. The attachment of the two beads to the ends, respectively, of the strand of the DNA can be confirmed by moving the focus position 55 for infrared laser beams and confirming that the right bead 53 is in synchronism with the movement of the focus position 55. The electromagnetic force is controlled for preventing excessive extension of the DNA molecule. When the strand 44 or 45 of λDNA is extended by the above method, its total length becomes about 16.5 μm and the extended strand is sufficiently inside the field of view of the microscope 51.2×51.2 μm. The stage of the microscope is slowly lowered to bring the sample DNA holding the bead at each end, close to the inner top surface of the cell. The stage is fixed just at the time when the bead or the DNA comes into contact with the top surface. In this case, the sample DNA is held within a distance of 0.1 μm or less from the top surface. Also in carrying out the polymerase reaction explained below, the λDNA is being captured by continuous action of laser beams of 1064 nm and the electromagnet which are used for fixing the beads attached to both ends, respectively.

Next, the phase-contrast microscope mode is switched over to a fluorescence microscope mode, and the beam splitter 30 shown in FIG. 10 is allowed to assume a non-mirror state, whereby the whole fluorescence is introduced into a cooled CCD camera 39. Circumstances near the microscope are those in a darkroom for the purpose of preventing light other than laser beams from being introduced into the cell. As shown in FIG. 14, a synthetic primer composed of an oligonucleotide having a length of 20 bases which is complementary to the base sequence of the oligonucleotide 47 introduced into the 5'-end of the sample DNA is introduced into the cell together with a buffer solution. The cell temperature is set at 30° C. and the primer is complementarily bonded to the 5'-end of the sample DNA. Subsequently, the cell temperature is set at 37° C., and a mixed buffer solution containing the 4 kinds of the chemically modified nucleotides shown in FIG. 16 to FIG. 19 and Sequenase Version 2.0 T7DNA polymerase (available from Amersham) is introduced into the cell. The environment of the sample DNA is always maintained as fresh composition of the mixed buffer solution by allowing the solution to flow continuously and slowly in one direction. The concentrations of all the 4 kinds of the chemically modified nucleotides are 100 nm and the polymerase concentration is 100 units/liter. All of these concentrations are about one-thousandth those employed in a conventional polymerase reaction. Sequenase Version 2.0 sold by Amersham has such a very great ability to elongate a complementary strand that the elongation rate is not less than 300-base length/second. Even at low concentrations of nucleotides of less than 100 nm, Sequenase Version 2.0 permits sufficient incorporation of the nucleotides, and causes very remarkable incorporation of nucleotide analogs such as the chemically modified nucleotides. The polymerase causes incorporation of, as a base next to the primer, only one base complementary to the base sequence of the sample DNA among the 4 kinds of the chemically modified nucleotides.

Figure 24:
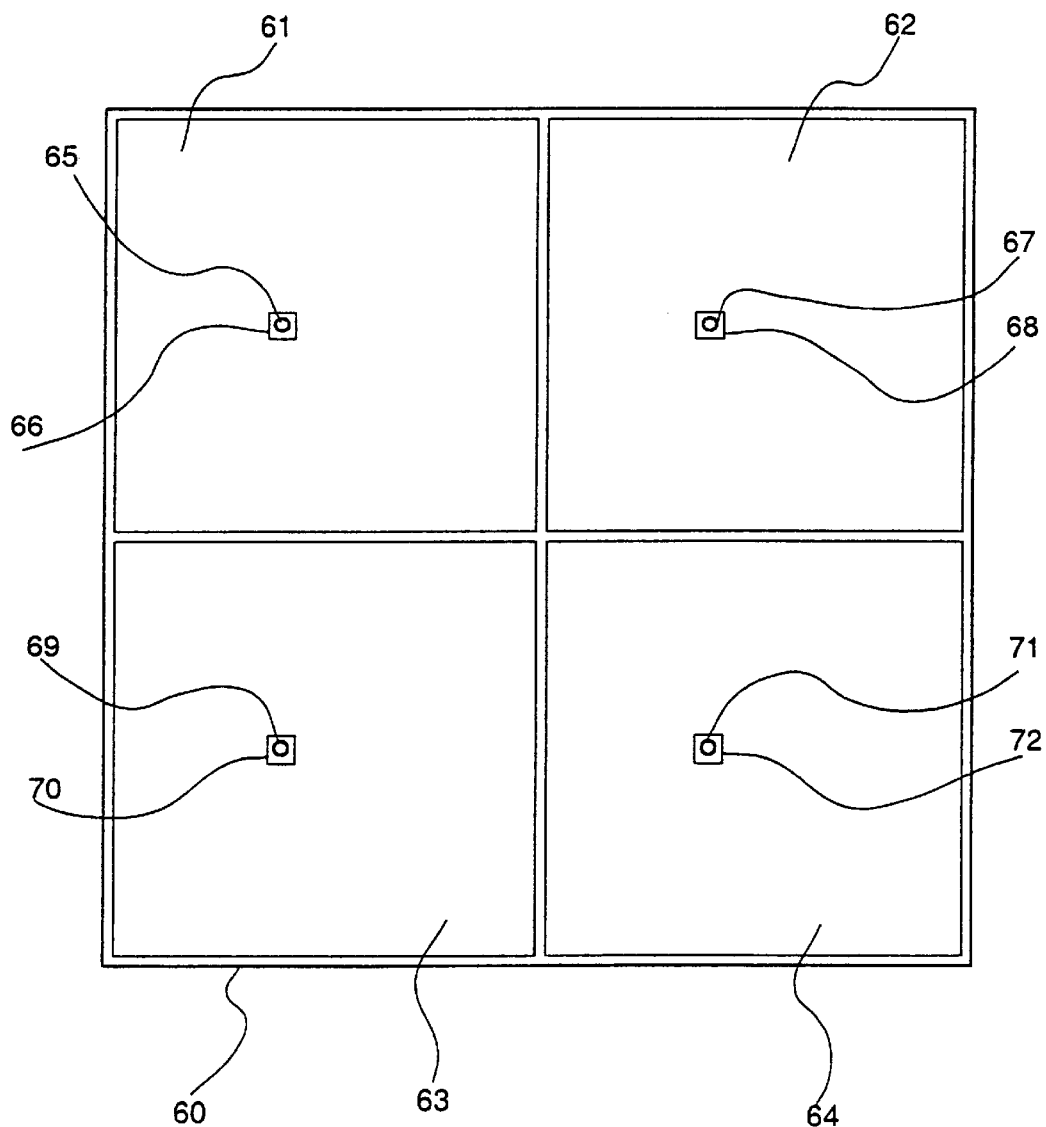
FIG. 24 is a schematic view of 4 divided images corresponding to a light emission spot in the field of view of the microscope in the example of the present invention.

Irradiation with laser beams of 488 nm and laser beams of 532 nm is carried out for 1 second, and light exposure is carried out in the cooled CCD camera 34 for 1 second in synchronism with the laser irradiation. Laser beams 21 are perfectly reflected from the inner top surface of the cell 25 and induce evanescent irradiation in a space in the cell which extends to 150 nm or less from the surface of the cell. Since the sample DNA is captured within a distance of 100 nm or less from the inner top surface of the cell, one of the chemically modified nucleotides which has been incorporated by the polymerase reaction is excited. Other molecules of the chemically modified nucleotides move about actively owing to Brownian motion and they are not detected even if they undergo the evanescent irradiation by accident. As shown in FIG. 24, for the whole field of view of 51.2×51.2 μm, the images detected by means of the cooled CCD camera 34 are displayed on a monitor 60 as first to fourth channels for the 4 divided images, respectively. The images (bright spots) 65, 67, 69 and 71 in the first to fourth channels which correspond to one light emission spot due to the chemically modified nucleotide incorporated are automatically recognized and detected.

Figure 8:
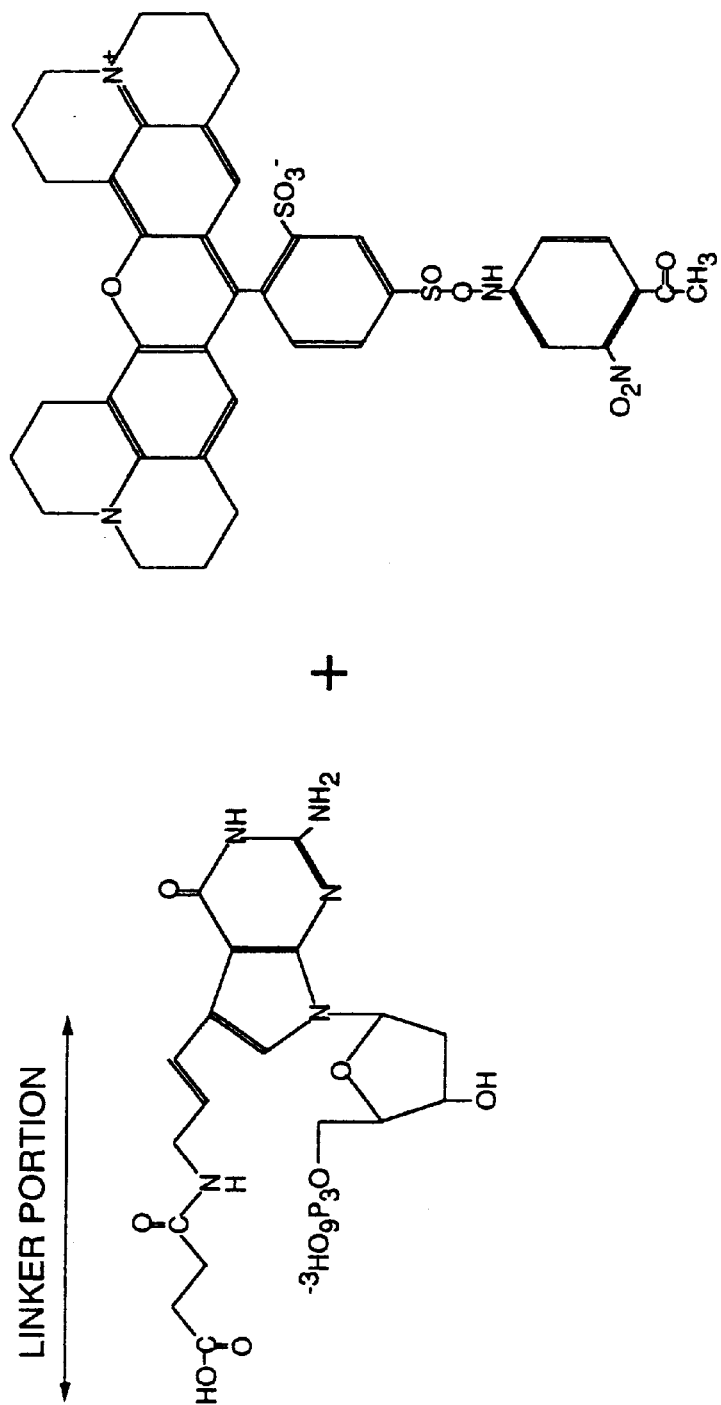
FIG. 8 is a scheme showing the photodecomposition of a Texas Red-labeled caged dGTP used in an example of the present invention.
Figure 9:
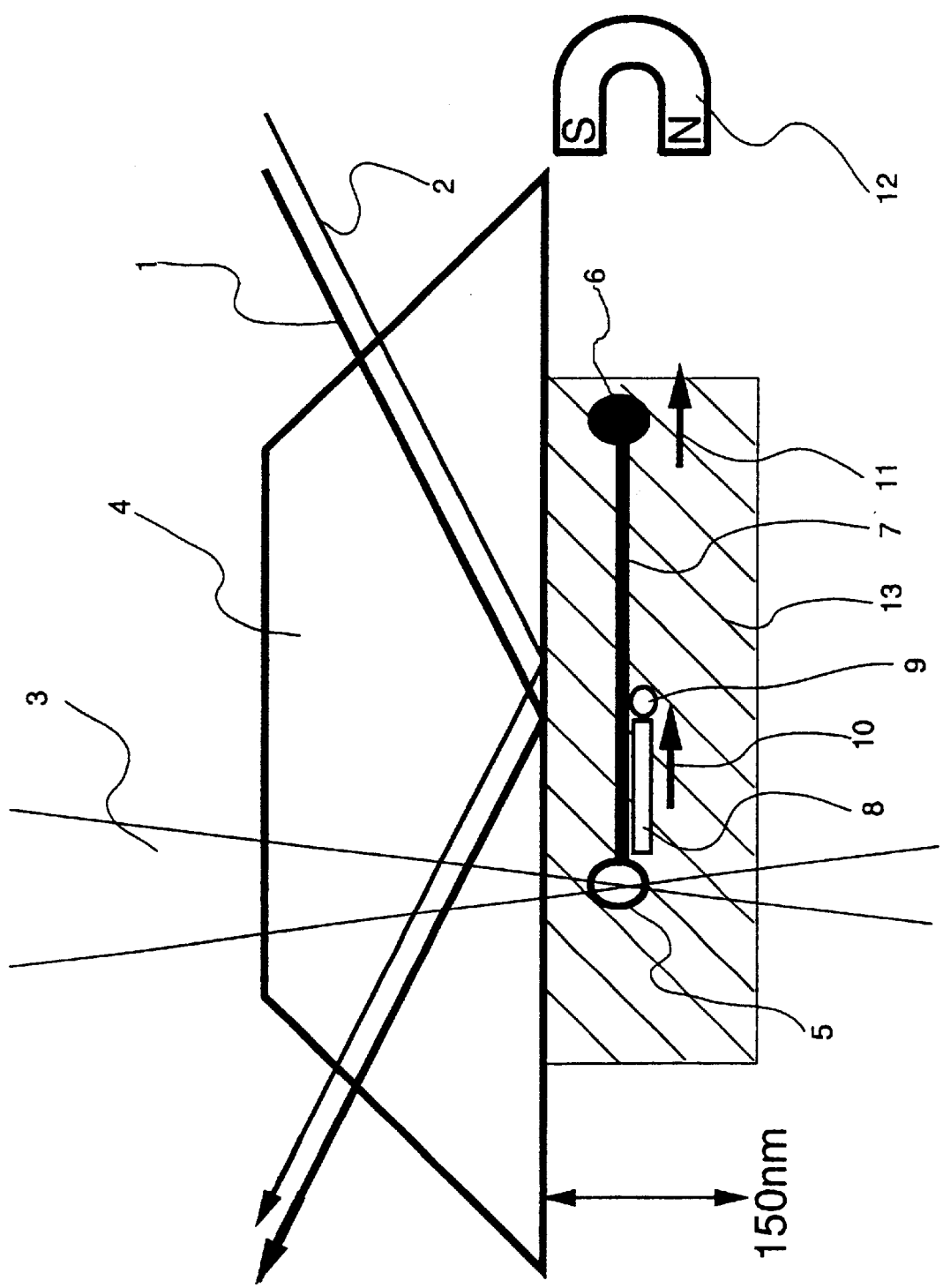
FIG. 9 is a schematic diagram showing an outline of the structure of the principal part of an apparatus for carrying out single-molecule measurement in the example of the present invention.

In the subsequent continuous measurement, as shown in FIG. 24, only luminance information in regions, respectively, near the above four spots, i.e., measurement regions 66, 68, 70 and 72 for the images in the first to fourth channels corresponding to the light emission spot are transferred to a computer, recorded and then analyzed. The 4 bright spots 65, 67, 69 and 71 change in position little by little with the lapse of time, and the 4 bright spots changing in position are automatically chased by a computer. The ratio among the fluorescence intensities of the 4 bright spots which correspond to fluorescence emission from one spot and are measured after the image division varies clearly depending on the spectrum of the fluorophore which has emitted fluorescence, i.e., the kind of this fluorophore. When the kind of the fluorophore is the same, the ratio among the fluorescence intensities of the 4 bright spots is constant. Therefore, the kind of the fluorophore can easily be determined from the ratio among the fluorescence intensities measured for the 4 bright spots. Then, irradiation with pulse oscillation ultraviolet laser beams of 355 nm is carried out for 10 nanoseconds. The laser beams are perfectly reflected from the internal top surface of the cell to induce evanescent irradiation in a space in the cell which extends to 150 nm or less from the surface. Since the sample DNA is captured within a distance of 100 nm or less from the inner top surface of the cell, the chemically modified nucleotide incorporated by the polymerase reaction is irradiated with ultraviolet light, so that the caged substance having the fluorophore attached thereto is released as shown in FIG. 8. Other molecules of the chemically modified nucleotides move about actively owing to Brownian motion, and the buffer solution is always allowed to flow so that even if any of these chemically modified nucleotides undergo the evanescent irradiation by accident and its caged substance is released, the released nucleotide may not be incorporated by the polymerase reaction. Subsequently, only one molecule of any of the chemically modified nucleotides is incorporated as the next into the complementary strand. Thereafter, the following procedure is repeated at regular time intervals. 0.4 second after the pulse oscillation of laser beams of 355 nm, irradiation with laser beams of 488 nm and laser beams of 532 nm is carried out for 0.5 second, and light exposure in the cooled CCD camera is carried out for 0.5 second in synchronism with the laser irradiation, after which the kind of fluorophore of the terminal chemically modified nucleotide incorporated by the elongation of the complementary strand is determined. Pulse oscillation of ultraviolet laser beams of 355 nm is carried out 0.1 second after completion of the irradiation with laser beams of 488 nm and laser beams of 532 nm to release the caged substance having the fluorophore attached thereto of the terminal chemically modified nucleotide incorporated by the elongation of the complementary strand, and the next chemically modified nucleotide is incorporated. The above cycle for 1.0 second in total inclusive of the data transfer time to the computer is repeated. Information concerning the fluorescence intensities of the 4 spots is transferred to the computer by utilizing a period of 0.5 second during which no light exposure is carried out. The kind of the base is determined by determining the kind of the fluorophore at once from the ratio among the fluorescence intensities of the 4 spots. The results of the base determination is outputted to the monitor in real time. By repeating the cycle capable of determining one base per second, the determination of the whole base sequence of λDNA having a length of 48502 bases can be completed in 48502 seconds, i.e., about 13.5 hours.

EXAMPLE 2

Figure 25:
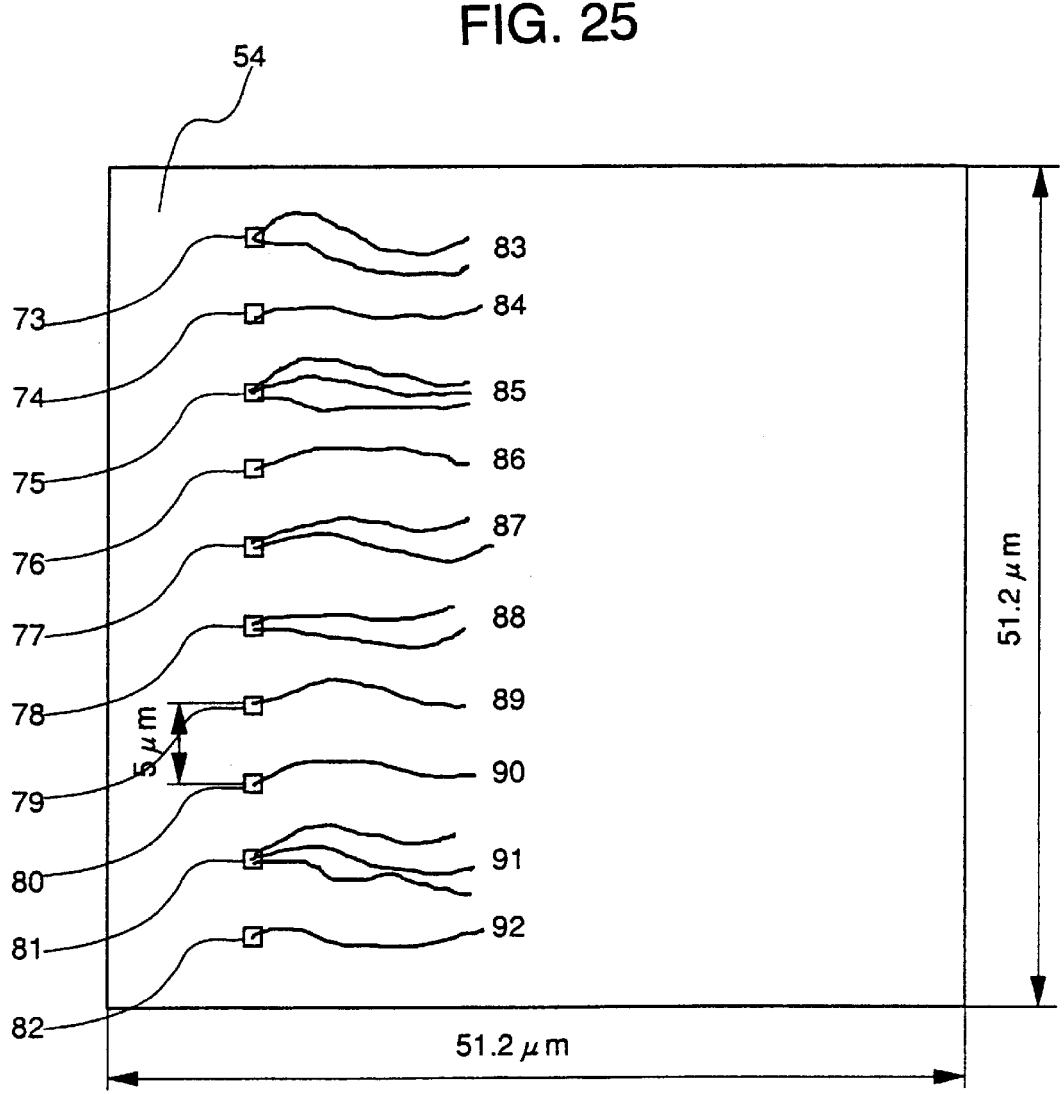
FIG. 25 is a diagram showing oligonucleotides complementary to 10 kinds of sample DNAs, respectively, which are fixed in the field of view of the microscope in another example of the present invention.

There is explained below the case of determining the base sequences of 10 kinds of DNA samples on a large scale at the same time. A synthetic oligonucleotide having a known base sequence is introduced into each end of each of 10 kinds of DNA samples having a length of 100 k bases, by ligation, and biotin is introduced into each 3'-end in the same manner as in Example 1. A known base sequence having a length of 50 bases is introduced into each 5'-end. This base sequence is varied depending on the 10 kinds of the DNA samples. On the other hand, streptavidin is attached to the outer surface of each magnetic polystyrene bead with a diameter of about 1 μm by acid amide linkage. Each of the DNA samples subjected to the ligation is denatured to assume a single-stranded state, and the magnetic bead is added to be attached to each 3'-end of each DNA sample. Measurement is carried out by using the same apparatus as in Example 1. As explained below, 10 kinds of single-stranded synthetic oligonucleotides are locally attached to the inner under surface of the cell. As shown in FIG. 25, on the 51.2×51.2 μm area of the glass surface of the cell which is the field of view of the microscope, single-stranded synthetic oligonucleotides 83 to 92 having a length of 50 bases which are complementary to the known base sequences, respectively, introduced into the 5'-ends of the first to tenth sample DNAs are linked to 10 fine sample-capturing regions 73 to 82 for capturing the first to tenth single-stranded sample DNAS, respectively. Each of the sample-capturing regions has an area of 1×1 μm and they are aligned in a straight line at 5-μm intervals. The first to tenth DNA samples carrying the different base sequences, respectively, at the 5'-end and the magnetic bead at the 3'-end are introduced into the cell as a mixture. The cell temperature is set at 25° C., and the sample DNAs are complementarily bonded to the oligonucleotides, respectively, having the complementary base sequences, respectively. Complementarily non-bonded molecules of the sample DNAs are removed from the field of view by allowing a buffer solution to flow. One to several sample DNAs are bonded to each sample-capturing region. Subsequently, a magnetic field is horizontally applied to apply a static magnetic force to the bead attached to the 3'-end of each sample DNA, whereby the first to tenth sample DNAs 93 to 102 are extended. The extending force is controlled by varying the intensity of the magnetic field. When the DNA samples having a length of 100 k bases are extended, their length becomes about 34 μm, and the 3'-end of each sample DNA is inside the field of view of 51.2 μm ×51.2 μm.

The cell temperature is set at 65° C. Since the complementary joint between each sample DNA and the oligonucleotide linked to the cell has a large length of 50 bases, it is maintained even at 65° C. A mixed buffer solution containing the 4 kinds of the chemically modified nucleotides shown in FIG. 27 to FIG. 30 (their fluorophores are indicated with abbreviations) and Ampli TaqDNA polymerase (available from TAKARA SHUZO Co., Ltd.) is introduced into the cell. In the chemically modified nucleotides shown in FIG. 27 to FIG. 30, the position of labeling a nucleotide with a caged substance having a fluorophore attached thereto is changed from a base to the carbon 3' position of ribose, unlike in the chemically modified nucleotides shown in FIG. 16 to FIG. 19, though the chemically modified nucleotides shown in FIG. 27 to FIG. 30 can be incorporated into a complementary strand by polymerase as in the case of using the chemically modified nucleotides shown in FIG. 16 to FIG. 19. Moreover, when the caged substance having a fluorophore attached thereto is released by ultraviolet irradiation according to the photoreaction shown in FIG. 1, the nucleotide becomes equivalent to that in unmodified state. The 4 kinds of the chemically modified nucleotides shown in FIG. 27 to FIG. 30 can be prepared by the same organic synthesis as in the case of the chemically modified nucleotides shown in FIG. 16 to FIG. 19. FIG. 27 to FIG. 30 show a caged dATP, caged dCTP, caged dGTP and caged dTTP, which are labeled with Cy 3.0. Cy 3.5, Cy 5.0 and Cy 5.5, respectively (mfd. by Biological Detection System, Inc.). By allowing the mixed buffer solution containing them to flow continuously and slowly in one direction, the environment of the sample DNAs is always maintained as fresh composition of the solution. Polymerase catalyzes the elongation reaction of a complementary strand using each oligonucleotide linked to the cell, as a primer. The subsequent continuous fluorescence measurement is the same as in Example 1 except for the following.

As fluorescence exciting laser beams, YAG laser beams (20 mW) of 532 nm and He—Ne laser beams (20 mW) of 633 nm are used. Interference filters corresponding to the four images have a transmission band with a transmittance of 70% or more in ranges of 540 to 580 nm, 580 to 620 nm, 650 to 680 nm, and 680 to 730 nm, respectively, and their transmittance outside the transmission band is $10^{-4}$ or less in a range of 300 to 1100 nm. Their transmittance at 355 nm, 532 nm and 633 nm, the wavelengths of laser beams is $10^{-6}$ or less. A metal thin film is formed by vapor deposition on the inner top surface of the cell, and plasma waves are caused in the metal by perfect reflection of laser beams to induce emission of near-field light by surface plasmons in the cell. The near-field light can be cast with high intensity on a region finer than in a method employing evanescent irradiation, so that single-molecule measurement can be realized by high-sensitivity fluorescence measurement.

Figure 26:
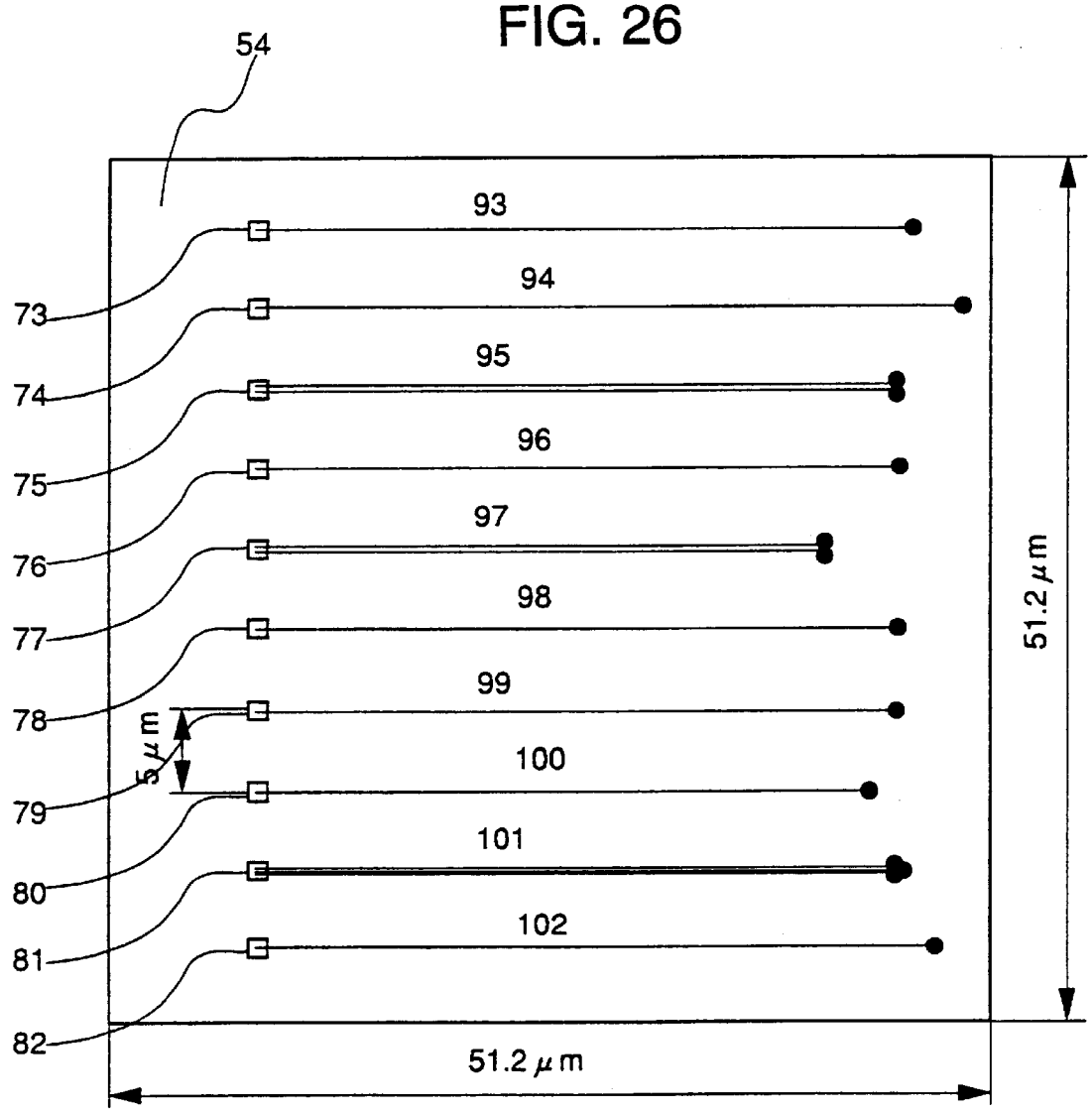
FIG. 26 is a schematic view of the 10 kinds of the sample DNAs captured in the cell by the use of the complementary oligonucleotides in the other example of the present invention.
Figure 27:
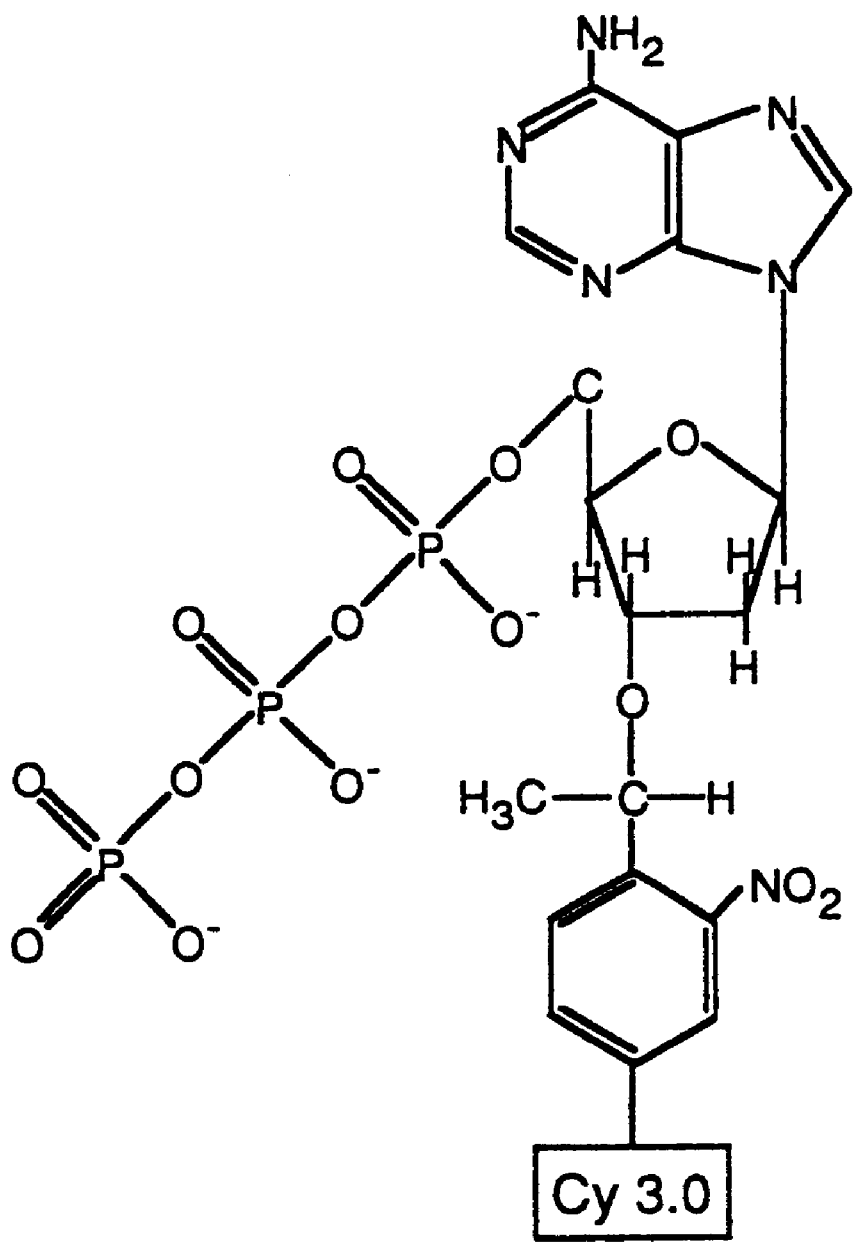
FIG. 27 is a diagram showing the structure of a fluorophore-labeled caged DATP used in the other example of the present invention.
Figure 28:
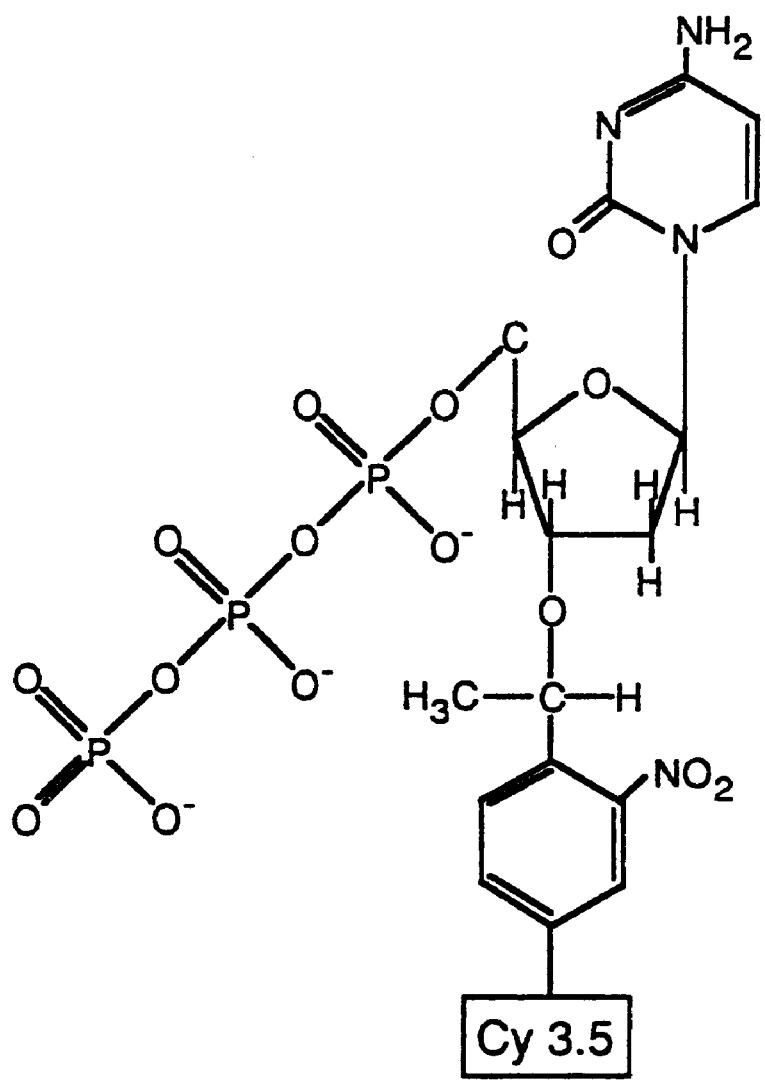
FIG. 28 is a diagram showing the structure of a fluorophore-labeled caged dCTP used in the other example of the present invention.
Figure 29:
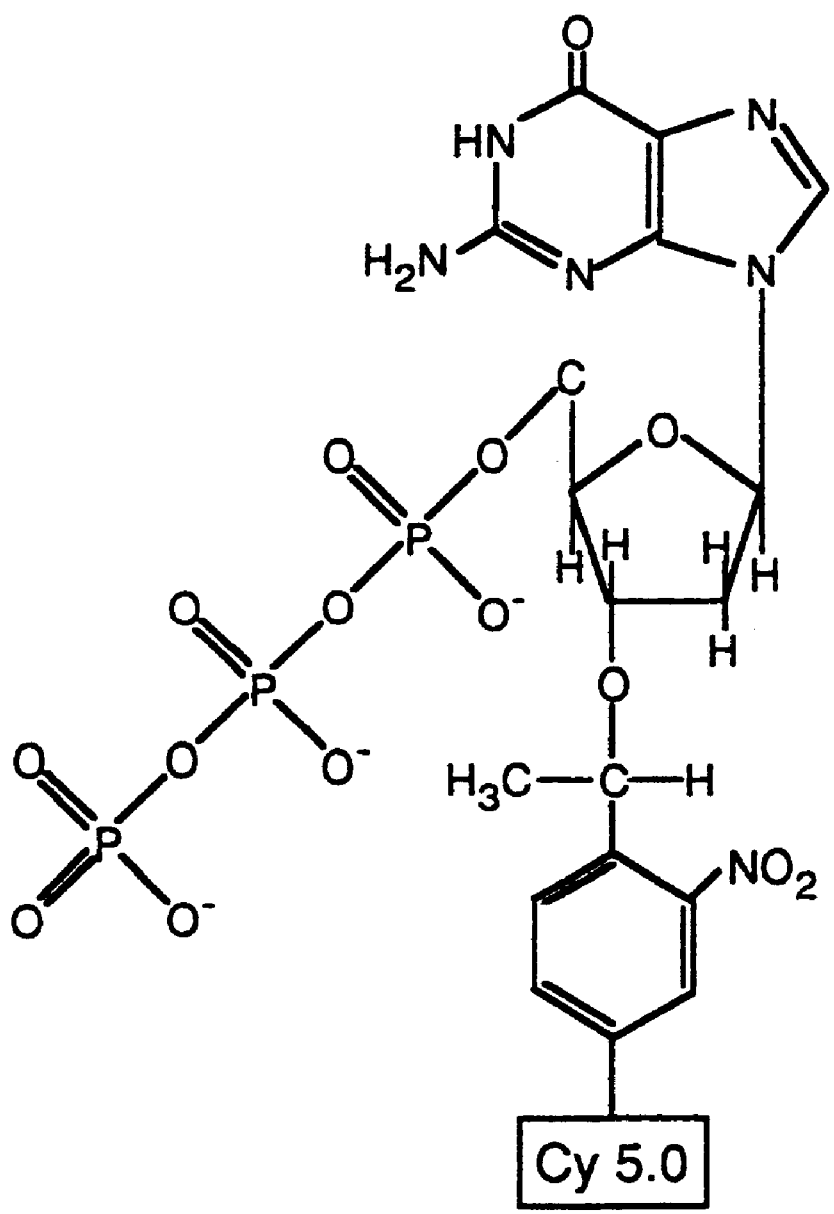
FIG. 29 is a diagram showing the structure of a fluorophore-labeled caged dGTP used in the other example of the present invention.
Figure 30:
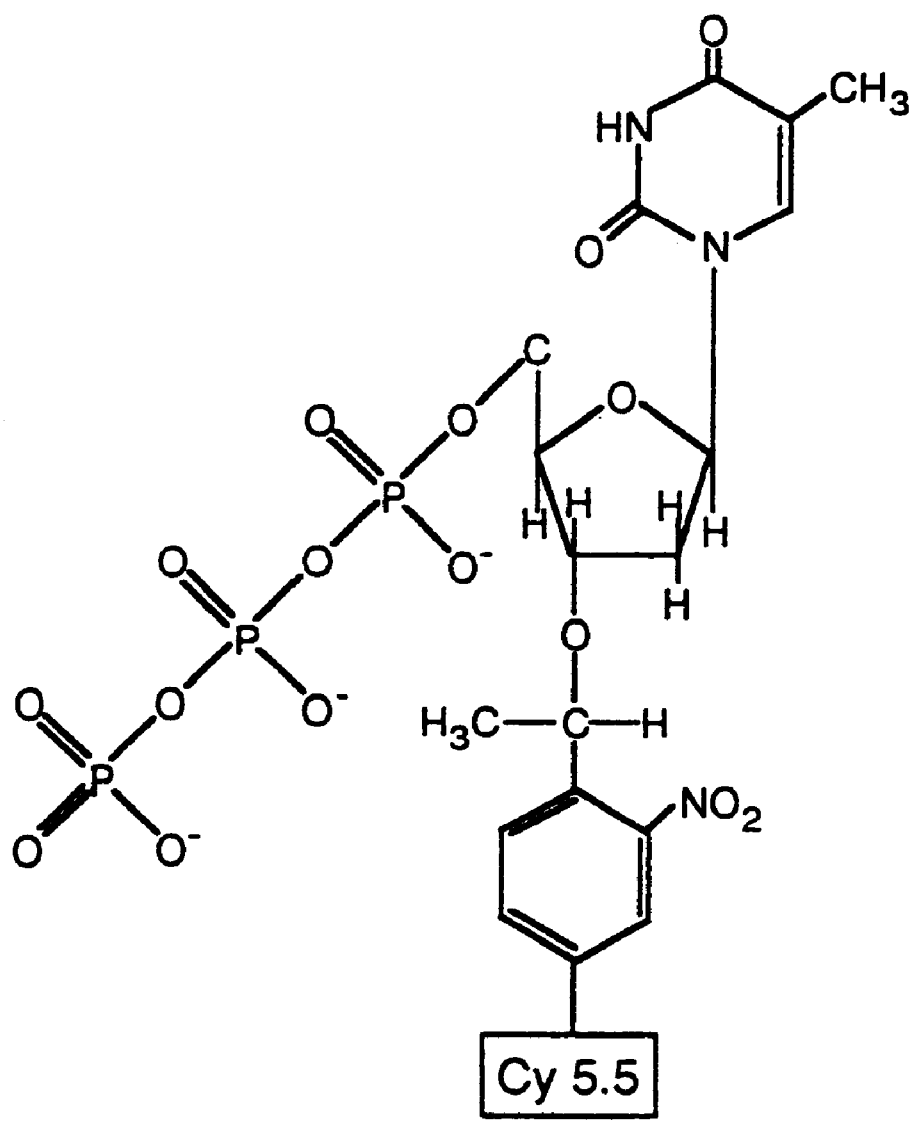
FIG. 30 is a diagram showing the structure of a fluorophore-labeled caged dTTP used in the other example of the present invention.
Figure 31:
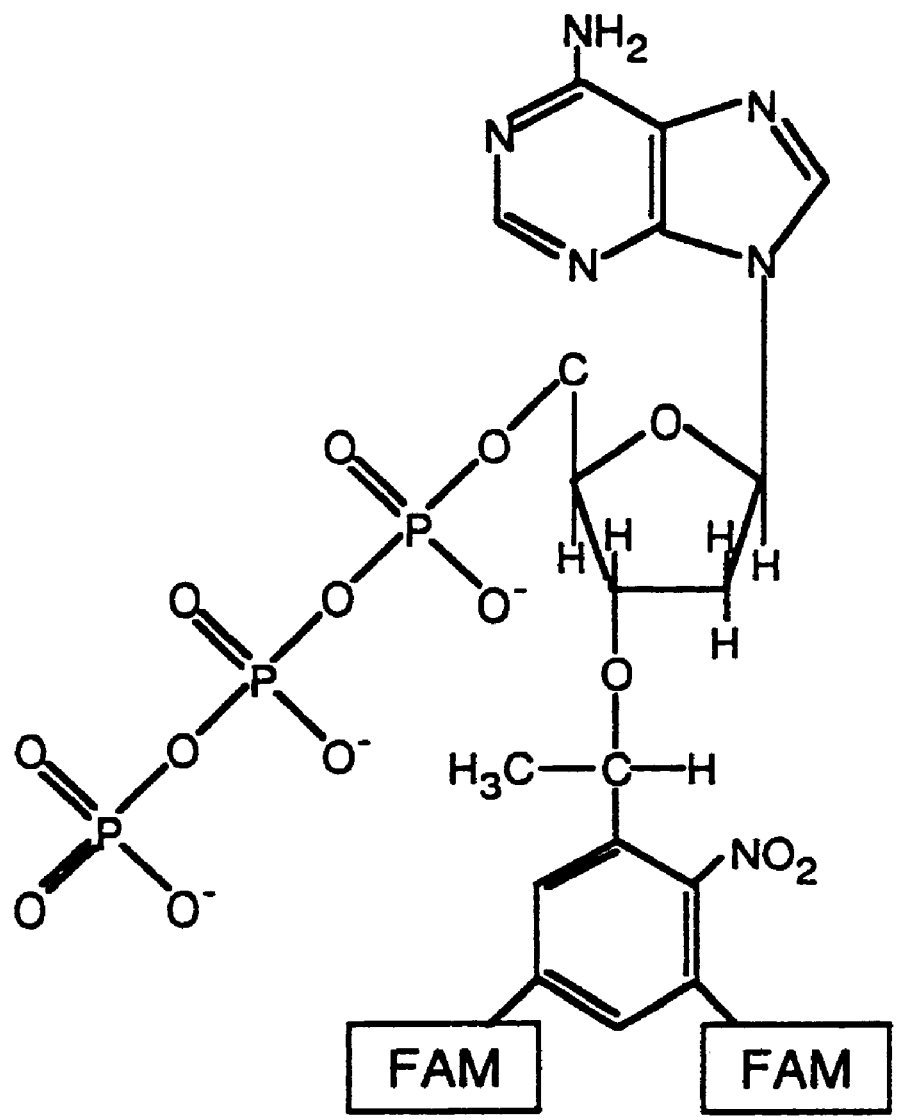
FIG. 31 is a diagram showing the structure of a fluorophore-labeled caged dATP use d in still another example of the present invention.
Figure 32:
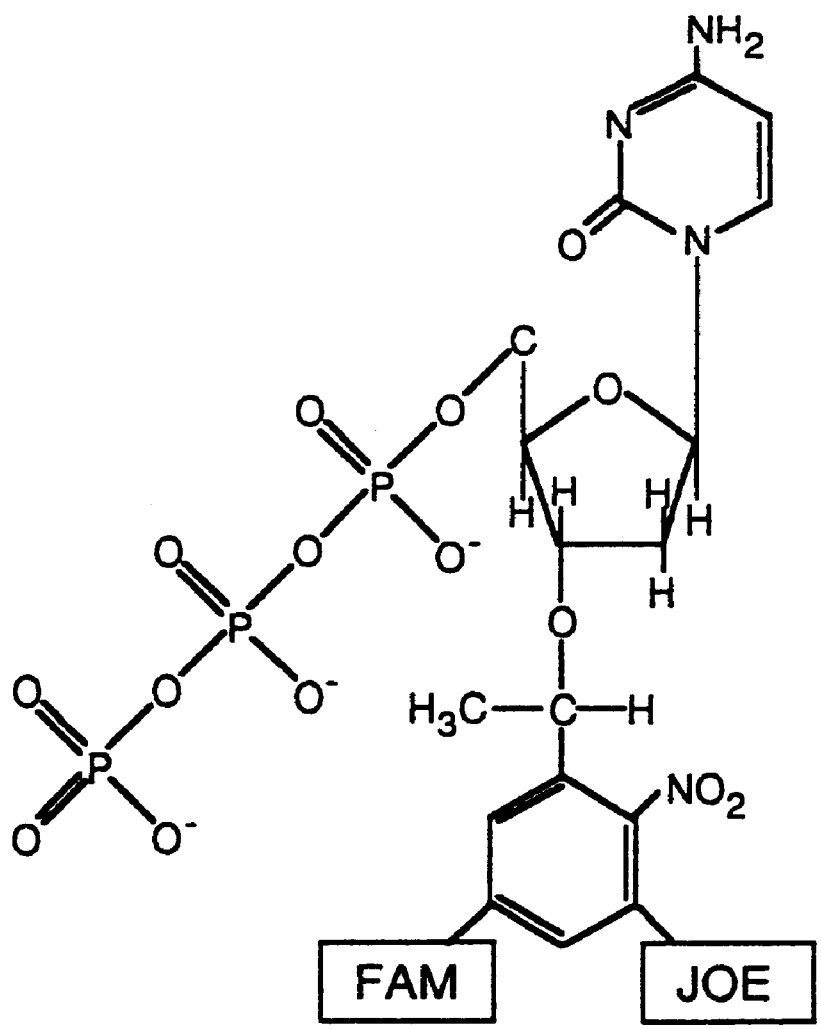
FIG. 32 is a diagram showing the structure of a fluorophore-labeled caged dCTP used in the still other example of the present invention.
Figure 33:
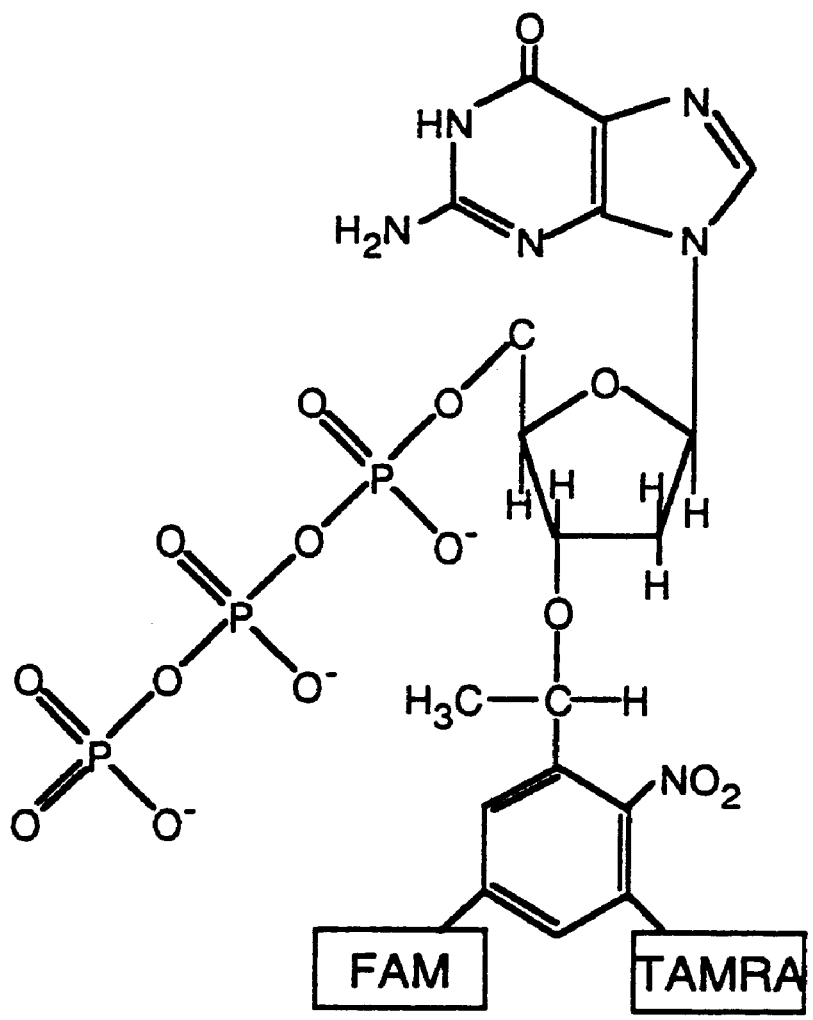
FIG. 33 is a diagram showing the structure of a fluorophore-labeled caged dGTP used in the still other example of the present invention.
Figure 34:
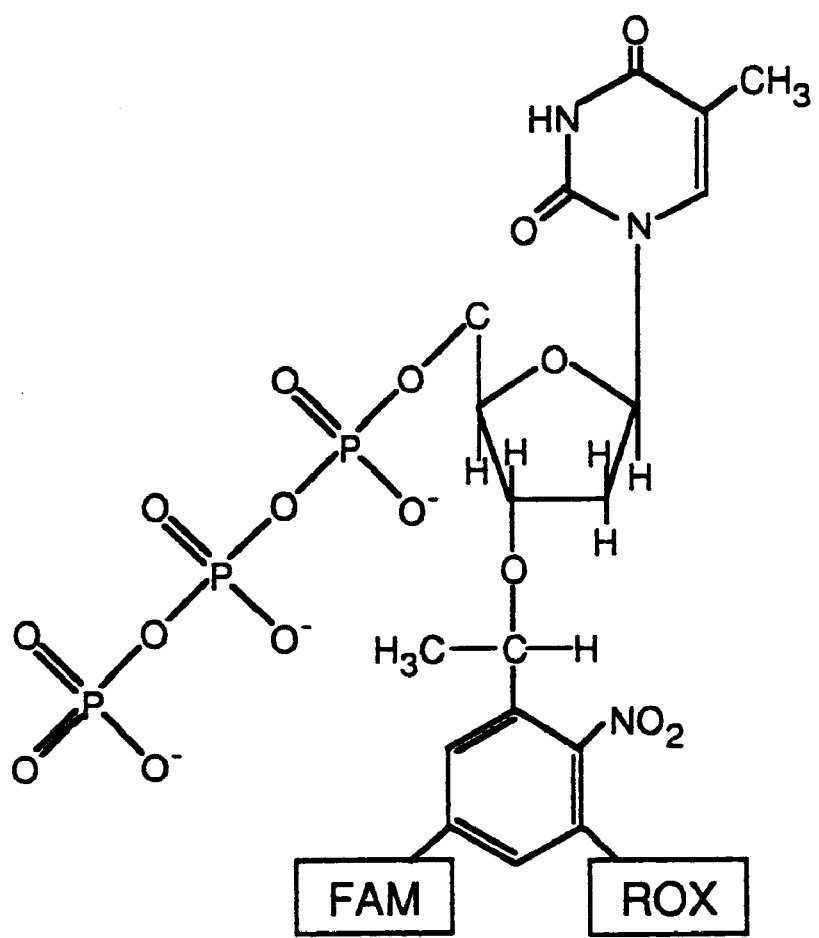
FIG. 34 is a diagram showing the structure of a fluorophore-labeled caged dTTP used in the still other example of the present invention.

For irradiating a molecule of the sample DNA with the near-field light due to surface plasmon resonance, the sample DNA is drawn toward the inner top surface of the cell by applying an electric field to the inside of the cell in an upward direction during a time period of 0.7 second in total composed of the time period of the irradiation with laser beams of 532 nm and laser beams of 633 nm, the time period of irradiation with laser beams of 355 nm and the time period between these time periods, in each cycle for 1.0 second which constitutes the continuous measurement. During the residual time period of 0.3 second, an electric field is applied in the opposite direction to keep away the sample DNA from the inner top surface of the cell and facilitate the incorporation of the next chemically modified nucleotide. The measuring points in the field of view are 10 points corresponding to the 10 samples, respectively, and the 10 points are divided each in four into 40 points as detected images, respectively. While chasing these 40 points as detected images, their fluorescence intensities are successively recorded and then analyzed. The 10 kinds of the sample DNAs are completely and spatially separated from one another as shown in FIG. 26, and hence can be independently subjected to the measurement. Depending on the sample DNA, a plurality of molecules thereof are captured, so that fluorescence from the plurality of the molecules is detected. However, since the fluorescence detected is always from the same fluorophore, only an increase in the fluorescence intensity is caused in the measurement and there is no problem at all. By carrying out the continuous measurement described above, one base is determined per second in each sample, so that the whole base sequences of the 10 samples each having a length of 100 k bases, i.e., the whole base sequences having a total length of 1 M base sequences can be determined mined in 100 k seconds, i.e., about one day.

EXAMPLE 3

In this example, the intracellular distribution of mRNAs is measured. About ten thousand kinds of mRNAs found in a specific kind of cells are extracted and then introduced into a fluorescence cell set under a fluorescence microscope. A measuring apparatus used in the present example is that obtained by modifying the measuring apparatus used in Example 2, as follows. As exciting laser beams, Ar ion laser beams of 488 nm are used in place of a combination of YAG laser beams of 532 nm and He—Ne laser beams of 633 nm. Four kinds of interference filters used in combination with a dividing-in-four prism have a transmission band with a transmittance of 70% or more in ranges of 500 to 540 nm, 540 to 570 nm, 570 to 590 nm, and 590 to 630 nm, respectively, and their transmittance outside the transmission band is $10^{-4}$ or less in a range of 300 to 1100 nm. At their transmittance at 355 nm and 488 nm, the wavelengths of the laser beams are $10^{-6}$ or less. Chemically modified nucleotides having the structures, respectively, shown in FIG. 31 to FIG. 34 are used. Each of them has two fluorophore labels attached to a nucleotide, unlike the chemically modified nucleotides shown in FIG. 27 to FIG. 30. FIG. 31 to FIG. 34 show a caged dATP, caged dCTP, caged dGTP and caged dTTP, respectively, which have FAM, JOE, TAMRA and ROX (mfd. by Applied Biosystems Inc.), respectively, as a label at the carbon 3 position of a nitrophenyl group bonded to the carbon 3 position of ribose. All of them have FAM as a label at the carbon 5 position of the nitrophenyl group. Energy transfer is caused between FAM and JOE, FAM and TAMRA, and FAM and ROX inside the nucleotides, respectively. Thus, not only FAM but also JOE, TAMRA and ROX can be very efficiently excited with Ar ion laser beams of 488 nm. Each fluorophore is bonded to nucleotide through the nitrophenyl group and released from the nucleotide by irradiation with ultraviolet pulse laser beams of 355 nm. Impurities such as unmodified nucleotides are previously removed by using a column or the like.

Figure 35:
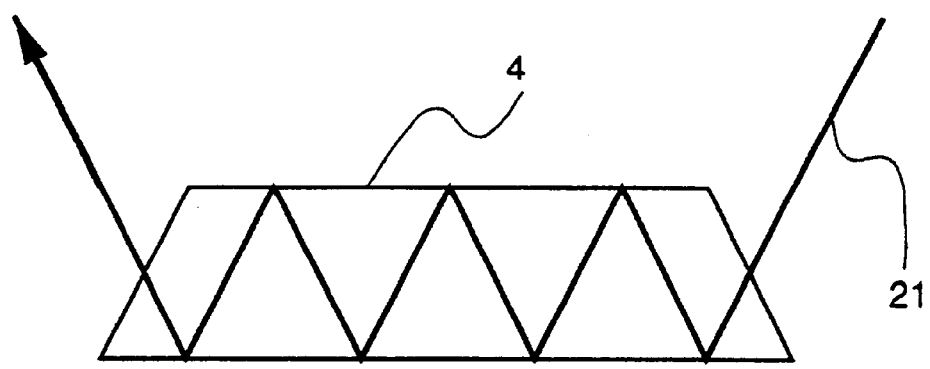
FIG. 35 is a diagram illustrating the multiple reflection of laser beams inside a prism used in the still other example of the present invention.
Figure 36:
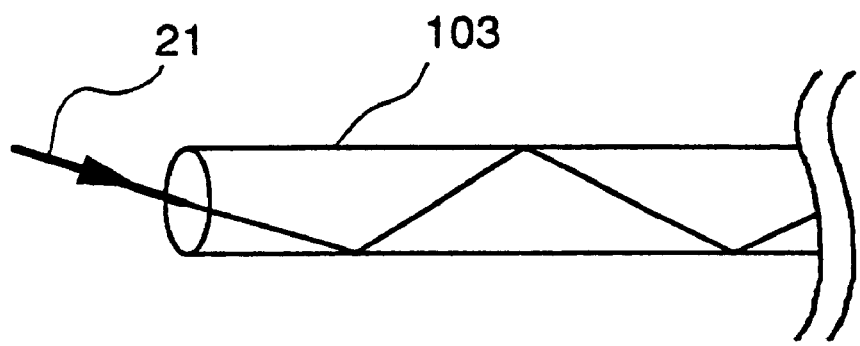
FIG. 36 is a diagram illustrating the multiple reflection of laser beams inside an optical fiber used in the still other example of the present invention.

As an objective lens, an oil-immersed 100- to 60-power lens (Plan-Apochromat×60, 1.40 NA, mfd. by Olympus Co., Ltd.) is used. As a photographing lens just in front of a camera, a 2.5- to 1.67-power lens (NFK×1.67, mfd. by Olympus Co., Ltd.) is used. The detection plane of the cooled two-dimensional CCD camera used has an area of 35.8×35.8 mm and is composed of 1024×1024 aligned picture elements each having an area of 35×35 $\mu$m. Since the image magnification on the image formation plane is 60×1.67, i.e., 100 times, each picture element corresponds to 0.35×0.35 $\mu$m. An image in the field of view of 179×179 $\mu$m is divided in four by a dividing-in-four prism inserted into the light path, and the resulting 4 divided images each having an area of 17.9×17.9 mm are projected on the detection plane to cover an area of 35.8×35.8 mm as in FIG. 13 so that they may not overlap with one another. In order to increase the intensity and uniformity of laser beams of 488 nm and 355 nm introduced into the 5 field of view of the microscope, there is adopted a multiple-reflection method comprising, as shown in FIG. 35, repeated perfect reflection of the introduced laser beams inside a prism. It is also possible to carry out measurement by, as shown in FIG. 36, introducing laser beams into an optical fiber 103, allowing them to reflect perfectly and repeatedly inside the fiber, and utilizing near-field light in the vicinity of the outer surface of the fiber. The measurement area can be broadened by bundling a large number of fibers and subjecting them to measurement at the same time. The 5'-end of a single-stranded synthetic oligonucleotide composed of a poly(T) labeled with FAM is linked to the inner under surface of the cell in the field of view of the microscope so that molecules of the oligonucleotide may be substantially uniformly linked at an average rate of 1 molecule per 10×10 $\mu$m area. The bonding positions in the field of view can be confirmed as fluorescence emission spots by irradiation with laser beams of 488 nm. The number of the emission spots, i.e., the number of poly(T) molecules bonded, in the field of view is about 330. The emission spots can be spatially separately detected and their fluorescences can be independently measured. There are recorded 1320 pairs of coordinates of images obtained by division in four on the detection plane which correspond to the 330 emission spots, and spots having the pairs, respectively, of coordinates are used as measuring points in the subsequent fluorescence measurement. The label FAM is decomposed to be faded, by continuous irradiation with laser beams of 488 nm at high output.

Each of the mRNAs introduced into the cell has a poly(A) portion, and hence the poly(A) portion binds complementarily to the fixed poly(T). Since this complementary binding takes place at random, the proportions of the mRNAs bonded complementarily to the 330 poly(T) molecules in the field of view which can be subjected to measurement at the same time reflect the intracellular frequency of occurrence and distribution of the mRNAs. Therefore, if the 330 mRNAs bonded can be identified, the kinds and amounts of the mRNAs found in the cells can be investigated. In the present example, the identification is realized by determining the base sequence of each mRNA directly and referring to an existing data base. When cDNA elongation reaction is carried out by using reverse transcriptase and the poly(T) as primer, direct base sequence determination using each mRNA as template is carried out in the same manner as in Example 2 except for using the chemically modified nucleotides shown in FIG. 31 to FIG. 34. Needless to say, it is also possible to synthesize cDNA previously and carry out base sequence determination by using the cDNA as a template. The mRNAs have 1 kilo bases to several kiros bases, and each of them has a length of 1 $\mu$m or less when extended. Therefore, during the elongation reaction of each complementary strand, the 330 emission spots do not overlap or interfere with one another because they are at an average distance of 10 $\mu$m or more from one another. The relative positions of the poly(A) and the poly(T) in the complementary bonding, i.e., the priming site in the elongation reaction of the complementary strand, vary at random depending on the 330 measuring positions. The indeterminacy of the priming site, however, does not matter because a signal obtained from each measuring position is information from a single molecule of each mRNA. This is the great merit of the base sequence determination method using a single molecule. The base sequence of each of the 330 kinds of the mRNAs is decoded at a speed of one base per second, so that the substantially whole base sequences of the mRNAs can be determined in 30 minutes or less. The base sequence information thus obtained is compared with the existing data base, whereby the kind of a protein coded for by each gene in the cell is determined and at the same time, the frequency distribution of the genes is displayed. Although the number of 330 is considered sufficient as a sampling number, the sampling number may, if necessary, be increased by repeating the above-mentioned measurement.

Although the poly(T) fixed on the cell is used as a primer in the present example, there may be used as a primer an oligonucleotide containing a base such as inosine, 3-nitropyrrole, 5-nitroindole or the like, which can bind complementarily to any of 4 kinds of bases (adenine, cytosine, guanine and thymine). Such an oligonucleotide can bind complementarily to any position of a template nucleic acid and permits elongation of a complementary strand starting from the binding position. As in the case of using the poly(T) as a primer, the indeterminacy of this starting point does not matter in the present example in which base sequence information is obtained from a single molecule of the template nucleic acid. Although the determination of base sequences of the mRNAs is described in the present example, the determination of base sequences of only tens or less bases is sufficient when mere mRNA distribution is measured. obtaining a base sequence not registered in the data base means the discovery of a novel gene. In addition to the advantages described above in Examples, the method of the present invention have the following advantages. The method permits investigation of the actions of polymerase and other various enzymes from elementary reactions and hence can contribute greatly to biochemistry, molecular biology, biophysics, medical science, etc. For example, the rate of an elementary reaction constituting the synthesis and elongation reaction of a complementary chain using polymerase, i.e., the rate of a reaction for the incorporation of a nucleotide or a chemically modified nucleotide can be measured, and the following, for instance, can be investigated in detail with high time-resolution capability: a manner in which the rate of the reaction for the incorporation varies depending on the kind of the nucleotide; a manner in which the rate of the reaction for the incorporation varies depending on the kind of the chemically-modifying substance of the chemically modified nucleotide; and a manner in which the reaction rate varies depending on the kind of the polymerase used for the synthesis and elongation reaction of the complementary chain.

According to the present invention, the base sequence of hundreds kilos or more bases of a single dna molecule can be determined, large-scale dna sequencing can be carried out rapidly and easily which has been very poor in efficiency and has required much time and labor, and pretreatment before the base sequence determination can be greatly simplified.

What is claimed is:

1. An apparatus for determining a base sequence of a template DNA comprising:
    a cell in which a complementary strand extension reaction using a polymerase is performed for extending a hybridized primer hybridized with a template DNA or extending an extended primer produced by said complementary strand extension reaction, by incorporating a single chemically modified nucleotide of four kinds of chemically modified nucleotides to 3'-terminus of said hybridized primer or said extended primer, in the presence of said four kinds of chemically modified nucleotides, wherein said single chemically modified nucleotide is complementary with a base sequence of said template DNA, and each of said four kinds of chemically modified nucleotides has a chemical modification for preventing a continuous progress of said complementary strand extension reaction, after incorporating said single chemically modified nucleotide to 3'-terminus of said hybridized primer or said extended primer;
    a laser which excites at least one fluorophore label included in said chemical modification of said chemically modified nucleotide incorporated to 3'-terminus of said hybridized primer or said extended primer;
    a lens which collects fluorescence emitted from said fluorophore label(s);
    filters, each of which selects a wavelength of said fluorescence;
    a photodetector which detects said fluorescence selected by said filters;
    an analyzer which determines a kind of a base of said chemically modified nucleotide incorporated to 3'-terminus of said hybridized primer or said extended primer, based on an output of said photodetector; and
    a light source which emits a light for releasing said chemical modification from said chemically modified nucleotide incorporated to 3'-terminus of said hybridized primer or said extended primer, in order to bring about a state at which said complementary strand extension reaction for extending said hybridized primer or said extended primer can proceed;
    wherein, by repeating said complementary strand extension reaction for extending said hybridized primer or said extended primer and releasing said chemical modification from said chemically modified nucleotide incorporated to 3'-terminus of said hybridized primer or said extended primer, said base sequence of said template DNA is determined one base by one base sequentially form the kinds of bases of said chemically modified nucleotides incorporated to said extended primer by said complementary strand extension reaction.

2. An apparatus according to claim 1, wherein said laser is used for an evanescence irradiation.

3. An apparatus according to claim 1, wherein said light source emits an ultraviolet light or an ultraviolet laser beam.

4. An apparatus according to claim 1, wherein said light is used for an evanescence irradiation, and by said evanescence irradiation, said chemical modification is released from said chemically modified nucleotide incorporated to 3'-terminus of said hybridized primer or said extended primer.

5. An apparatus according to claim 1, wherein a plurality of kinds of said template DNA are captured in different portions of said cell, and the base sequences of said template DNAs are determined at the same time.

6. An apparatus according to claim 1, wherein the base sequences of different portions of said DNA template are determined at the same time.

7. An apparatus according to claim 1, wherein said DNA template is attached to a solid support and said solid support is captured in said cell.

8. An apparatus according to claim 1, wherein said template DNA is captured in said cell.

9. An apparatus for determining a base sequence of a template DNA comprising:
    a cell which holds a template DNA hybridized with a primer, wherein a buffer solution including four kinds of caged nucleotides flows into said cell, and wherein a complementary strand extension reaction using a polymerase is performed for extending said hybridized primer or an extended primer produced by said complementary strand extension reaction, by incorporating a single caged nucleotide of four kinds of caged nucleotides to 3'-terminus of said hybridized primer or said extended primer, in the presence of said four kinds of caged nucleotides, said single caged nucleotide is complementary with a base sequence of said template DNA, and each of four kinds of caged nucleotides has at least one fluorophore label and a continuous progress of said complementary strand extension reaction is prevented after incorporating said single caged nucleotide 3'-terminus of said hybridized primer or said extended primer;
    a laser which excites said fluorophore label(s) of said caged nucleotide incorporated to 3'-terminus of said hybridized primer or said extended primer;
    a lens which collects fluorescence emitted from said fluorophore label(s);
    filters, each of which selects a wavelength of said fluorescence;
    a photodetector which detects said fluorescence selected by said filters;

an analyzer which determines a kind of a base of said caged nucleotide incorporated to 3'-terminus of said hybridized primer or said extended primer, based on an output of said photodetector; and a light source which emits a light for releasing said fluorophore label(s) from said caged nucleotide incorporated to 3'-terminus of said hybridized primer or said extended primer, in order to bring about a state at which said complementary strand extension reaction for extending said hybridized primer or said extended primer can proceed;

wherein by repeating said complementary strand extension reaction for extending said hybridized primer or said extended primer and releasing said fluorophore label(s) from said caged nucleotides incorporated to 3'-terminus of said hybridized primer or said extended primer, said base sequence of said template DNA is determined one base by one base sequentially form the kinds of bases of said caged nucleotides incorporated to said extended primer by said complementary strand extension reaction.

* * * * *